(12) United States Patent
Safai et al.

(10) Patent No.: US 8,836,934 B1
(45) Date of Patent: Sep. 16, 2014

(54) CONTAMINATION IDENTIFICATION SYSTEM

(75) Inventors: Morteza Safai, Newcastle, WA (US); Kimberly D. Meredith, Newcastle, WA (US)

(73) Assignee: The Boeing Company, Chicago, IL (US)

( * ) Notice: Subject to any disclaimer, the term of this patent is extended or adjusted under 35 U.S.C. 154(b) by 158 days.

(21) Appl. No.: 13/472,031

(22) Filed: May 15, 2012

(51) Int. Cl.
*G01N 21/00* (2006.01)

(52) U.S. Cl.
USPC ............................................... 356/237.3

(58) Field of Classification Search
CPC ....... G01N 21/00; G01N 21/25; G01N 21/35; G01N 2021/8472
USPC ....................................... 356/237.3
See application file for complete search history.

(56) References Cited

U.S. PATENT DOCUMENTS

| | | | | |
|---|---|---|---|---|
| 5,016,099 A | * | 5/1991 | Bongardt et al. | 348/128 |
| 5,159,185 A | * | 10/1992 | Lehr | 250/205 |
| 5,495,429 A | * | 2/1996 | Craven et al. | 702/127 |
| 6,064,429 A | * | 5/2000 | Belk et al. | 348/128 |
| 7,171,033 B2 | * | 1/2007 | Engelbart et al. | 382/141 |
| 7,495,758 B2 | | 2/2009 | Walton | |
| 7,712,502 B2 | * | 5/2010 | Engelbart et al. | 156/351 |
| 8,068,659 B2 | * | 11/2011 | Engelbart et al. | 382/141 |
| 8,184,281 B2 | * | 5/2012 | Engelbart et al. | 356/237.1 |
| 8,207,508 B2 | | 6/2012 | Lawless | |
| 2008/0055591 A1 | | 3/2008 | Walton | |
| 2008/0267472 A1 | | 10/2008 | Demos | |
| 2009/0223635 A1 | | 9/2009 | Lawless | |

FOREIGN PATENT DOCUMENTS

EP 0903574 A2 3/1999

OTHER PUBLICATIONS

Brelstaff et al., Hyper-spectral clamera system:—acquisition and analysis, SPIE, Geographic Information Systems, Photogrammetry, and Geological/Geophysical Remote Sensing, vol. 2587, Nov. 1995, pp. 150-160.

"Powerful & Precise Hyperspectral Measurements for Field Research," ASD, Inc., 1 page, accessed Sep. 9, 2011, http://discover.asdi.com/FieldSpec3_hh2_promo/?utm_campaign.

"Analyzing Hyperspectral Images Tutorial", MicroImages, Inc., May 2011, pp. 1-40.

(Continued)

*Primary Examiner* — Roy M Punnoose
(74) *Attorney, Agent, or Firm* — Yee & Associates, P.C.

(57) ABSTRACT

A method and apparatus for inspecting a composite workpiece. A response to electromagnetic radiation directed to a surface of the composite workpiece is separated into a number of wavelengths for each of a number of locations on the surface of the composite workpiece. A set of contaminants on the surface of the composite workpiece is identified from the number of wavelengths for the each of the number of locations. A two-dimensional image of the surface of the composite workpiece is generated with a set of graphical indicators indicating the set of contaminants identified from the number of wavelengths for the each of the number of locations on the surface of the composite workpiece.

20 Claims, 14 Drawing Sheets

(56) References Cited

OTHER PUBLICATIONS

Diaz et al., "Hyperspectral system for the detection of foreign bodies in meat products", Proceedings Eurosensors XXV, Procedia Engineering, vol. 25, Sep. 2011, pp. 313-316.

Garcia-Allende et al., "Hyperspectral imaging sustains production-process competitiveness", SPIE Newsroom, Apr. 2010, pp. 1-4.

"Multispectral/Hyperspectral Array Configurations", using Wedge Imaging Spectrometer technology, (Elerding et al.) Proceedings of the SPIE, vol. 1479, Aug. 1991, 1 page.

PCT search report dated May 21, 2013 regarding application PCT/US2013/025980, international filing date Feb. 13, 2013, applicant reference 11-1536-PCT, applicant The Boeing Company, 10 pages.

* cited by examiner

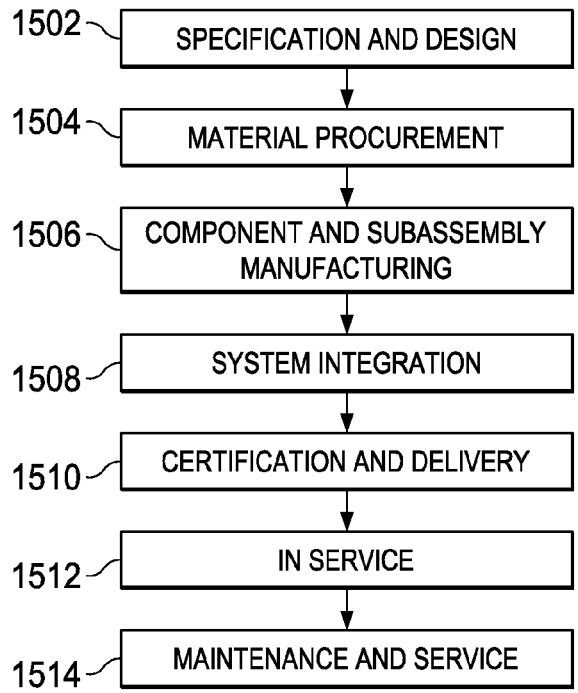
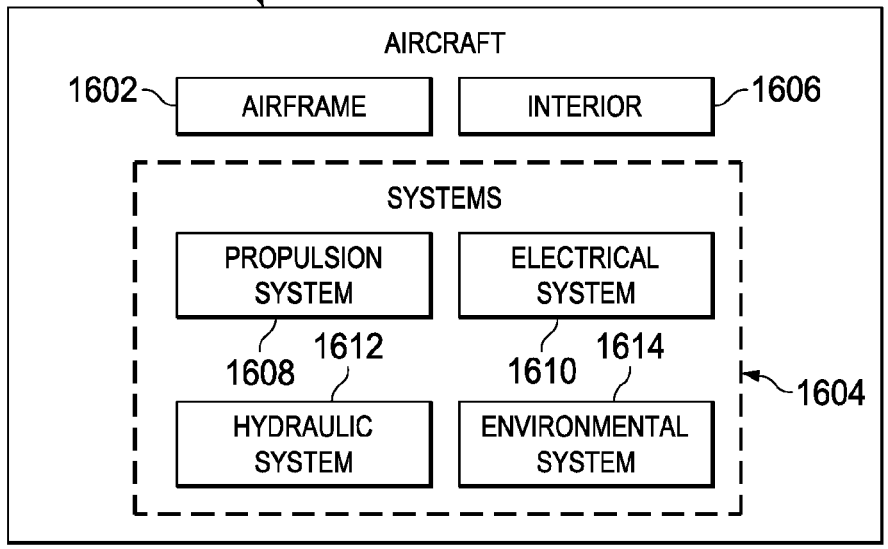

US 8,836,934 B1

CONTAMINATION IDENTIFICATION SYSTEM

BACKGROUND INFORMATION

1. Field

The present disclosure relates generally to manufacturing composite structures and, in particular, to inspecting composite workpieces during manufacturing. Still more particularly, the present disclosure relates to a method and apparatus for identifying contaminants on composite workpieces prior to curing the composite workpieces to form composite structures.

2. Background

Aircraft are being designed and manufactured with greater and greater percentages of composite materials. Composite materials are used in aircraft to decrease the weight of the aircraft. This decreased weight improves performance features such as payload capacities and fuel efficiencies. Further, composite materials provide longer service life for various components in an aircraft.

Composite materials are tough, light-weight materials created by combining two or more functional components. For example, a composite material may include reinforcing fibers bound in polymer resin matrix. The fibers may be unidirectional or may take the form of a woven cloth or fabric. The fibers and resins are arranged and cured to form a composite material.

Further, using composite materials to create aerospace composite structures potentially allows for portions of an aircraft to be manufactured in larger pieces or sections. For example, a fuselage in an aircraft may be created in cylindrical sections to form the fuselage of the aircraft. Other examples include, without limitation, wing sections joined to form a wing or stabilizer sections joined to form a stabilizer.

In manufacturing composite structures, layers of composite material are typically laid up on a tool. The layers may be comprised of fibers in sheets. These sheets may take the form of fabrics, tape, tows, or other suitable forms. In some cases, resin may be infused or preimpregnated into the sheets. These types of sheets are commonly referred to as prepreg.

The different layers of prepreg may be laid up in different orientations and different numbers of layers may be used depending on the thickness of the composite structure being manufactured. These layers may be laid up by hand or using automated lamination equipment such as a tape laminating machine or a fiber placement system.

After the different layers have been laid up on the tool, the layers consolidated and cured upon exposure to temperature and pressure, thus forming the final composite structure. Thereafter, the composite structure may be inspected to determine whether inconsistencies are present. The inspection may be performed using x-ray inspection systems, ultrasound inspection systems, and other types of non-destructive inspection systems.

If an inconsistency is identified, the composite structure may be reworked. In some cases, the inconsistency may result in the composite structure being discarded, requiring new composite structure to be manufactured. Examples of inconsistencies that may be present in a composite structure include voids, porosity, delamination, foreign object debris (FOD), and other types of inconsistencies.

Reworking parts or discarding and remanufacturing composite structures may delay the completion of an aircraft using the composite structures. Further, reworking or discarding parts may increase the cost in manufacturing aircraft by an undesirable amount.

Therefore, it would be desirable to have a method and apparatus that takes into account at least one of the issues discussed above as well as possibly other issues.

SUMMARY

In one illustrative embodiment, a method for inspecting a composite workpiece is present. A response to electromagnetic radiation directed to a surface of the composite workpiece is separated into a number of wavelengths for each of a number of locations on the surface of the composite workpiece. A set of contaminants on the surface of the composite workpiece is identified from the number of wavelengths for the each of the number of locations. A two-dimensional image of the surface of the composite workpiece is generated with a set of graphical indicators indicating the set of contaminants identified from the number of wavelengths for the each of the number of locations on the surface of the composite workpiece.

In another illustrative embodiment, a method for inspecting a tool for laying up layers of composite material is present. A response to electromagnetic radiation directed to a surface of the tool is separated into a number of wavelengths for each of a number of locations on the surface of the tool prior to laying up the layers of composite material on the surface of the tool. A set of contaminants is identified from the number of wavelengths for the each of the number of locations on the surface of the tool. A two-dimensional image of the surface of the tool is generated with a set of graphical indicators indicating the set of contaminants identified from the number of wavelengths for the each of the number of locations on the surface of the tool.

In still another illustrative embodiment, a method for inspecting a composite material is present. A response to electromagnetic radiation directed to a surface of the composite material is separated into a number of wavelengths for each of a number of locations on the surface of the composite material. A set of inconsistencies for the composite material is identified from the number of wavelengths for the each of the number of locations. A two-dimensional image of the composite material with a set of graphical indicators indicating the set of inconsistencies identified from the number of wavelengths for the each of the number of locations on the surface of the composite material is generated.

In yet another illustrative embodiment, an apparatus comprises a spectral sensor system and an analyzer. The spectral sensor system is configured to separate a response to electromagnetic radiation directed at a surface of a composite workpiece into a number of wavelengths and generate data from the number of wavelengths of the electromagnetic radiation. The analyzer is configured to cause the spectral sensor system to generate the data from the response after a number of layers of composite material have been laid up for the composite workpiece and prior to the number of layers of composite material being cured. The analyzer is further configured to generate a two-dimensional image of the surface of the composite workpiece with a set of graphical indicators indicating a set of contaminants identified from the number of wavelengths for each of a number of locations on the surface of the composite workpiece.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and advantages thereof, will best be understood by reference to the following detailed description of an illustrative embodiment of the present disclosure when read in conjunction with the accompanying drawings, wherein:

FIG. 15 is an illustration of an aircraft manufacturing and service method in accordance with an illustrative embodiment; and FIG. 16 is an illustration of an aircraft in which an illustrative embodiment may be implemented.

DETAILED DESCRIPTION

Figure 1:
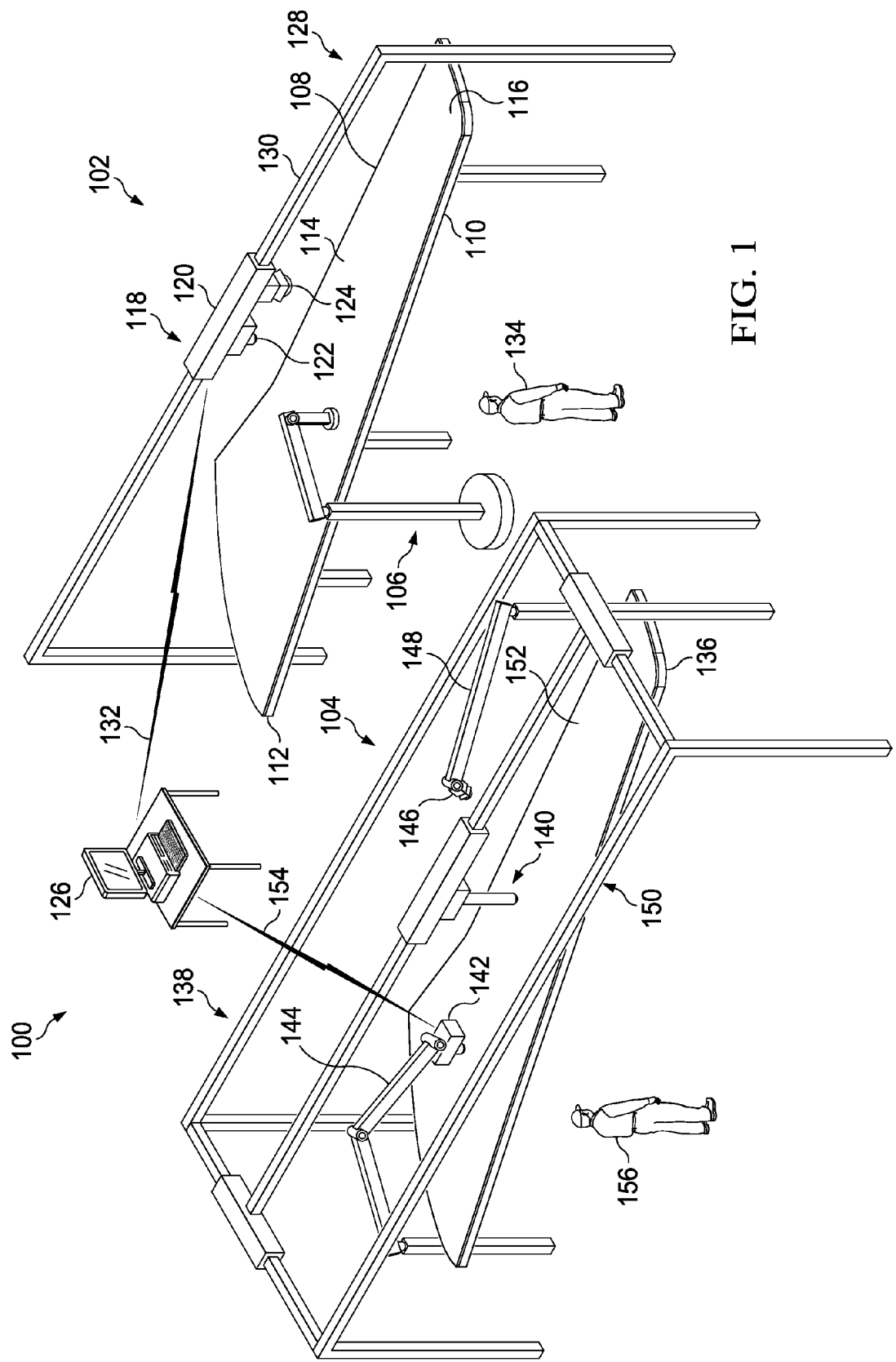
FIG. 1 is an illustration of a manufacturing environment in accordance with an illustrative embodiment.

The different illustrative embodiments recognize and take into account one or more different considerations. For example, the illustrative embodiments recognize and take into account that inconsistencies may be caused by contaminants during the manufacturing of a composite structure. For example, as layers of composite material are being laid up on a workpiece, contaminants may be present on the surface of one of the layers of composite material. These contaminants may already be present on the layer of composite material, originate from the manufacturing environment as the layer is placed on the workpiece, or come from some other source.

As additional layers of composite material are placed on top of the layers on which contaminants are present, the contaminants become embedded between layers of composite material. The illustrative embodiments also may recognize and take into account that contaminants may be present on the surface of a tool on which the layers of composite material are laid up. These contaminants may adhere to a layer of composite material that is placed on the surface of the tool. When the contaminants take the form of liquids, these contaminants soak into one or more layers of composite material.

These contaminants may result in inconsistencies when the composite workpiece with these layers is cured. For example, without limitation, contaminants may result in undesired levels of at least one of voids, porosity, delaminations, and other types of inconsistencies. As used herein, the phrase "at least one of", when used with a list of items, means different combinations of one or more of the listed items may be used and only one of each item in the list may be needed. For example, "at least one of item A, item B, and item C" may include, without limitation, item A or item A and item B. This example also may include item A, item B, and item C, or item B and item C.

The illustrative embodiments recognize and take into account that the presence of these contaminants on the surface of the layers of composite material laid up on a composite workpiece for a composite structure may be, for example, without limitation, particles, debris, liquids, moisture, and other types of undesirable contaminants. The illustrative embodiments recognize and take into account that identifying a presence of these contaminants on the surface of layers of composite material prior to curing the layers may reduce the amount of rework and the number of composite structures that are discarded. Further, when the number of composite structures discarded is reduced, the number of replacement composite structures manufactured also is reduced.

The illustrative embodiments also recognize and take into account that these contaminants are often not visible to the naked eye. Consequently, inspecting the layers of composite materials for contaminants may be more difficult than desired during manufacturing of composite structures from the layers of composite materials.

Thus, the illustrative embodiments provide a method and apparatus for inspecting composite workpieces. In these illustrative examples, a composite workpiece may be a number of layers of composite material that have been laid up for a composite structure. The process may direct electromagnetic radiation to a surface of the composite workpiece. A response to the electromagnetic radiation directed at the surface of the composite workpiece is separated into a number of wavelengths for each of a number of locations on the surface.

A two-dimensional image of the surface of the composite workpiece is generated with a set of graphical indicators indicating a set of contaminants identified from the number of wavelengths for each of the set of locations. As used herein, a "set of" when used with reference to items means zero, one, or more items. For example, a set of contaminants is zero or more contaminants. In other words, a set of contaminants may sometimes be an empty set when contaminants are not identified. The two-dimensional image may be used to determine whether contaminants are present and to identify where action should be taken if contaminants are present.

Turning now to FIG. 1, an illustration of a manufacturing environment is depicted in accordance with an illustrative embodiment. In this depicted example, manufacturing environment 100 includes composite layup station 102 and composite layup station 104.

Composite layup station 102 and composite layup station 104 are stations at which layers of composite material may be laid up when manufacturing composite structures. In this illustrative example, composite layup system 106 may place layers of composite material 108 onto tool 110 for composite workpiece 112 at composite layup station 102. In this illustrative example, composite layup system 106 is a robotic arm on which an end effector is present for laying up layers of composite material 108.

In these illustrative examples, inspection of surface 114 of layer 116 in layers of composite material 108 is made prior to curing layers of composite material 108. In this illustrative example, the inspection may be made using inspection system 118.

Inspection system 118 comprises housing 120, imaging system 122, light source 124, and computer 126. Housing 120 is moveable on platform 128. In this illustrative example, platform 128 includes rail system 130 and housing 120. Housing 120 in platform 128 holds imaging system 122 and light source 124.

Light source 124 is configured to direct light to locations on surface 114 of composite workpiece 112. In particular, light is directed to surface 114 of layer 116 in layers of composite material 108 that form composite workpiece 112.

Imaging system 122 is configured to receive a response to the light directed by light source 124 onto locations on surface 114 of composite workpiece 112. Imaging system 122 is configured to separate the response for each location on surface 114 into a number of wavelengths. This data is sent to computer 126. In other words, a response may be detected for each location and a number of wavelengths generated for that particular location from the response detected. In this illustrative example, the data is sent from imaging system 122 to computer 126 over wireless communications link 132.

Computer 126 identifies any contaminants that may be present at the locations using the data. Computer 126 is configured to generate a two-dimensional image of surface 114. In the illustrative examples, the two-dimensional image may be a two-dimensional spectrogram response of surface 114. The image may include graphical indicators indicating contaminants identified using the data for each of the locations.

This image may be used by operator 134 to identify any contaminants that may be present on surface 114 of composite workpiece 112. Further, the image also may be used to identify the locations at which contaminants are present on surface 114 of composite workpiece 112.

In these illustrative examples, this identification of the contaminants is performed prior to curing composite workpiece 112. In this manner, the contaminants may be removed from composite workpiece 112. For example, the contaminants may be particles that are removed. In other examples, if the contaminants cannot be removed from composite workpiece 112, one or more layers of composite material 108 may be replaced such that the contaminants are no longer present.

In another illustrative example, composite layup station 104 includes tool 136 and composite layup system 138. In this illustrative example, composite layup system 138 includes a platform on which a composite layup unit may move relative to tool 136 to lay up layers of composite material on tool 136.

In this illustrative example, inspection system 140 includes imaging system 142 associated with robotic arm 144 and light source 146 associated with robotic arm 148. Robotic arm 144 and robotic arm 148 form platform 150 for inspection system 140 in this illustrative example. Inspection system 140 also includes computer 126.

When one component is "associated" with another component, the association is a physical association in these depicted examples. For example, a first component, imaging system 142, may be considered to be associated with a second component, robotic arm 144, by being secured to the second component, bonded to the second component, mounted to the second component, welded to the second component, fastened to the second component, and/or connected to the second component in some other suitable manner. The first component also may be connected to the second component using a third component. The first component may also be considered to be associated with the second component by being formed as part of and/or an extension of the second component.

Robotic arm 148 moves light source 146 to direct light to different locations on surface 152 of tool 136 in these illustrative examples. Imaging system 142 may be moved by robotic arm 144 to detect a response to the light directed to surface 152 of tool 136 for each of the locations on surface 152. In a similar fashion, imaging system 142 generates data comprising a number of wavelengths for one of the locations on surface 152 on tool 136.

This data is sent to computer 126 over wireless communications link 154. Computer 126 analyzes this data to determine whether contaminants are present on surface 152 of tool 136. Computer 126 is also configured to generate a two-dimensional image of surface 152 of tool 136. The two-dimensional image also may include graphical indicators identifying any contaminants that have been detected on surface 152 of tool 136.

Operator 156 may use this image to determine whether contaminants are present. Further, operator 156 may remove the contaminants from surface 152 of tool 136 prior to using composite layup system 138 to layup composite material on tool 136. Contaminants on surface 152 of tool 136 may be transferred onto one or more layers of composite materials laid up on surface 152. These contaminants may also result in inconsistencies when the layers of composite materials are cured to form the composite structure.

By inspecting surface 152 of tool 136 prior to laying up composite materials on surface 152 of tool 136, contaminants on surface 152 of tool 136 may be identified and removed. As a result, the occurrence of inconsistencies on a composite structure caused by contaminants on surface 152 of tool 136 may be reduced.

In this manner, issues with contaminants causing inconsistencies in composite structures may be reduced. By performing inspections prior to curing composite workpiece 112, the composite structure resulting from composite workpiece 112 is less likely to have inconsistencies as compared to currently used manufacturing processes for composite structures.

Figure 2:
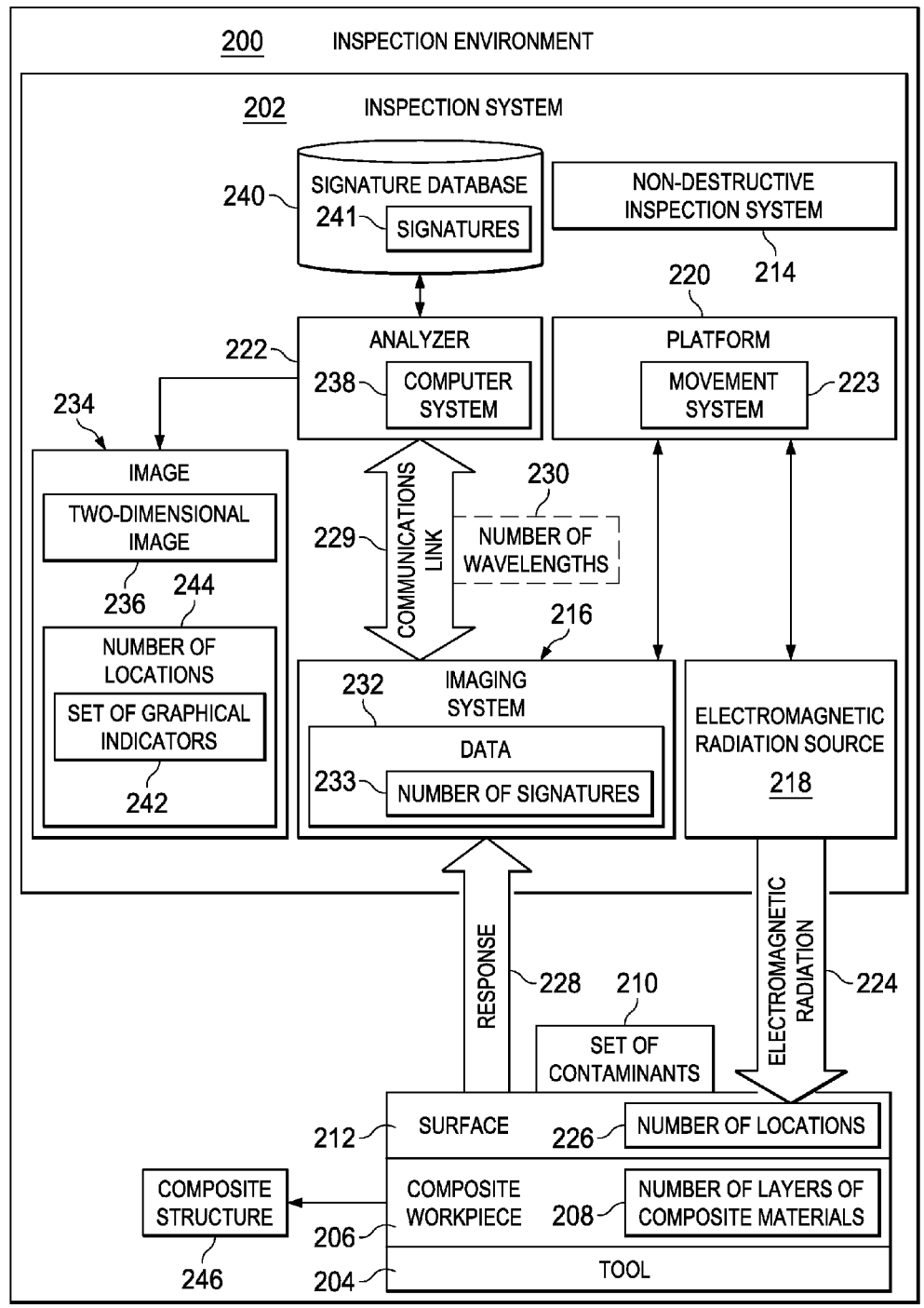
FIG. 2 is an illustration of a block diagram of an inspection environment in accordance with an illustrative embodiment.

Turning now to FIG. 2, an illustration of a block diagram of an inspection environment is depicted in accordance with an illustrative embodiment. Inspection system 118 and inspection system 140 in manufacturing environment 100 are examples of physical implementations for components in inspection environment 200 in FIG. 2.

In this illustrative example, inspection system 202 in inspection environment 200 may be used to perform inspection of tool 204, composite workpiece 206, or both tool 204 and composite workpiece 206.

In these illustrative examples, number of layers of composite materials 208 forms composite workpiece 206. Number of layers of composite materials 208 is laid up on tool 204 during manufacturing of composite workpiece 206.

In these illustrative examples, set of contaminants 210 may be present on surface 212 of composite workpiece 206. In other words, set of contaminants 210 is present on surface 212 on number of layers of composite materials 208. In these illustrative examples, set of contaminants 210 is present on surface 212 of a layer of composite material that is not covered by another layer of composite material in number of layers of composite materials 208.

In these illustrative examples, an inspection of surface 212 of number of layers of composite materials 208 may be performed prior to curing composite workpiece 206. In particular, this inspection may be performed before additional layers of composite materials are placed on top of surface 212 of number of layers of composite materials 208.

As depicted, the inspection may be performed using inspection system 202, which takes the form of non-destructive inspection system 214 in these illustrative examples. Inspection system 202 may include imaging system 216, electromagnetic radiation source 218, platform 220, and analyzer 222.

Platform 220 is a hardware system that may include software. Platform 220 may be stationary or may be mobile.

Imaging system 216 and electromagnetic radiation source 218 may be associated with platform 220. In some illustrative examples, analyzer 222 also may be associated with platform 220. Platform 220 provides support for these and any other components.

Additionally, platform 220 may be configured to move components associated with platform 220 such as, for example, imaging system 216 and electromagnetic radiation source 218. As depicted, platform 220 may include movement system 223 configured to move at least one of platform 220 and composite workpiece 206.

Electromagnetic radiation source 218 is a hardware device and may include software. Electromagnetic radiation source 218 is configured to generate electromagnetic radiation 224. Electromagnetic radiation source 218 is configured to direct electromagnetic radiation 224 to number of locations 226 on surface 212 of composite workpiece 206.

In these illustrative examples, electromagnetic radiation source 218 may take various forms. For example, without limitation, electromagnetic radiation source 218 may be a laser system, a halogen light system, a light emitting diode system, a xenon arc lamp system, a laser diode system, a tunable laser system, a quartz lamp system and other suitable types of electromagnetic radiation sources. Electromagnetic radiation 224 may be at least one of visible light, infrared light, and other suitable types of electromagnetic radiation.

Imaging system 216 is a hardware device and may include software. Imaging system 216 is configured to receive and process response 228. Response 228 is a response to electromagnetic radiation 224 directed to number of locations 226 on surface 212 of composite workpiece 206. Response 228 to electromagnetic radiation 224 directed to surface 212 of composite workpiece 206 is separated into number of wavelengths 230 for each of number of locations 226.

Data 232 is generated by imaging system 216 from response 228. For example, data 232 includes data generated from number of wavelengths 230 separated out from response 228 for each of number of locations 226. In these illustrative examples, data 232 includes an intensity for each wavelength in number of wavelengths 230 for a particular location in number of locations 226. The portion of data 232 for a particular location in number of locations 226 forms a signature in these examples. Thus, number of signatures 233 may be present for number of locations 226 in data 232.

Data 232 is sent from imaging system 216 to analyzer 222 over communications link 229. Communications link 229 may be a wired communications link, a wireless communications link, an optical communications link, or some other suitable type of communications link.

Analyzer 222 is a hardware device and may include software. In these illustrative examples, analyzer 222 may be implemented using computer system 238. Computer system 238 is comprised of a number of computers. When more than one computer is present, those computers may be in communication with each other using a communications medium such as a network.

Analyzer 222 is configured to generate image 234 using data 232. Image 234 may be displayed by computer system 238. Image 234 may be displayed using a display device such as a liquid crystal display or other suitable type of display device. In these illustrative examples, image 234 takes the form of two-dimensional image 236.

In these illustrative examples, analyzer 222 identifies set of contaminants 210 on surface 212 of composite workpiece 206. As discussed above, set of contaminants 210 may be an empty set in which no contaminants are present.

Analyzer 222 identifies set of contaminants 210 using signature database 240. For example, analyzer 222 compares data 232 to signature database 240 to determine whether contaminants are present. More specifically, number of signatures 233 is compared to signatures 241 in signature database 240. In these illustrative examples, signature database 240 is a database of wavelengths for known contaminants.

Signatures 241 contain information materials. These materials may include at least one of contaminants, composite materials expected to be present, and other materials. In these illustrative examples, a signature of a material comprises a number of intensities for a number of wavelengths that is present for the contaminant. The intensities for different wavelengths for a material form the signature for that particular material. These intensities at the different wavelengths are unique for a material in these illustrative examples.

As a result, the intensities for the number of wavelengths 230 in data 232 may be compared to signatures 241 to determine whether a contaminant is present. Signature database 240 also may be used to identify materials that are expected to be present in composite workpiece 206.

Thus, analyzer 222 may also identify the types of composite materials used in number of layers of composite materials 208. In this manner, analyzer 222 may also determine whether number of layers of composite materials 208 is the desired type of composite materials for use in composite workpiece 206.

In these illustrative examples, set of graphical indicators 242 are included in image 234. Set of graphical indicators 242 are used to identify set of contaminants 210 for each of number of locations 226 on surface 212 of composite workpiece 206. In other words, each location in number of locations 226 may have no contaminants, or one or more contaminants.

In these illustrative examples, set of graphical indicators 242 is included in number of locations 244 in image 234 corresponding to number of locations 226 on surface 212 of composite workpiece 206. In other words, a graphical indicator in set of graphical indicators 242 used to identify a contaminant in set of contaminants 210 may be placed in a location within number of locations 244 in image 234 such that the location corresponds to the location in number of locations 226 on surface 212 where the contaminant is present.

In other words, the placement of set of graphical indicators 242 in number of locations 244 are such that an operator may identify the corresponding locations in number of locations 226 when looking at surface 212 of composite workpiece 206. Further, set of graphical indicators 242 also may include graphical indicators that indicate an absence of a contaminant on surface 212 in some illustrative examples.

Additionally, in some illustrative examples, analyzer 222 may project image 234 onto surface 212 of composite workpiece 206. This projection of image 234 may be performed by imaging system 216. The projection of image 234 onto surface 212 of composite workpiece 206 is such that set of graphical indicators 242 is displayed on set of contaminants 210 on surface 212 of composite workpiece 206. In these illustrative examples, set of graphical indicators 242 may have a one to one ratio such that the graphical indicators show the actual size of contaminants within set of contaminants 210 when image 234 with set of graphical indicators 242 is projected onto surface 212 of composite workpiece 206.

In these illustrative examples, the steps of separating response 228 into number of wavelengths 230 for each of number of locations 226 on surface 212, identifying set of contaminants 210 from number of wavelengths 230 for each of number of locations 226 on surface 212, and generating image 234 are performed when number of layers of composite materials 208 are laid up for composite workpiece 206. In particular, these steps are performed prior to curing composite workpiece 206 to form composite structure 246. In these illustrative examples, composite structure 246 may be a composite aircraft part. These steps may be performed each time one or more layers of composite materials are laid up for composite workpiece 206.

By inspecting surface 212 prior to curing composite workpiece 206, contaminants may be found through the inspection before curing composite workpiece 206 to form composite structure 246. When contaminants are identified before curing composite workpiece 206, the contaminants may be removed. The removal of contaminants may be, for example, removing particles, evaporating liquids, or other suitable operations. In some illustrative examples, the contaminants may be removed by replacing one or more of the number of layers of composite materials 208 on which contaminants are identified.

Figure 3:
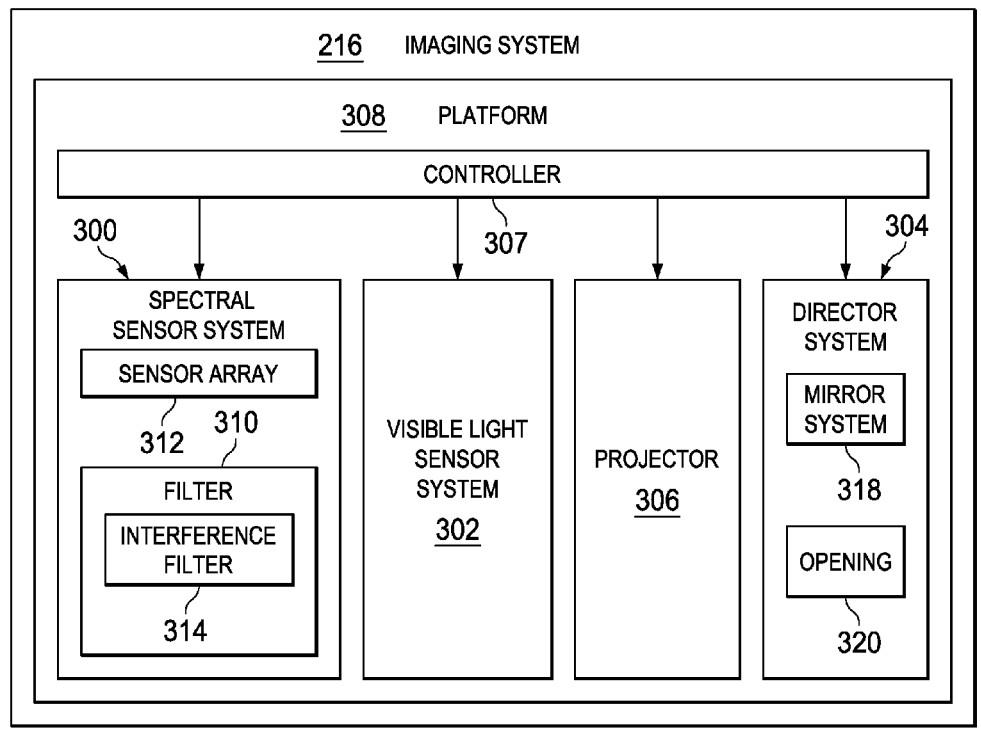
FIG. 3 is an illustration of a block diagram of an imaging system in accordance with an illustrative embodiment.

Turning now to FIG. 3, an illustration of a block diagram of an imaging system is depicted in accordance with an illustrative embodiment. In this illustrative example, components that may be used in imaging system 216 in FIG. 2 are shown. As depicted, imaging system 216 includes spectral sensor system 300, visible light sensor system 302, director system 304, projector 306, controller 307, and platform 308.

In these illustrative examples, spectral sensor system 300, visible light sensor system 302, director system 304, projector 306, and controller 307 are associated with platform 308. Platform 308 is a structure that may take various forms. For example, without limitation, platform 308 may be at least one of a frame, a rail system, a housing, a robotic arm, and some other suitable type of structure. For example, platform 308 may be a housing in which one or more of these different components in imaging system 216 may be located.

Spectral sensor system 300 is a hardware system and is configured to receive response 228 and generate data 232 for number of wavelengths 230 from FIG. 2. In these illustrative examples, spectral sensor system 300 is configured to generate number of wavelengths 230 in the form of a range of wavelengths. This range of wavelengths may be continuous or may include gaps depending on the particular implementation.

Spectral sensor system 300 includes filter 310, and sensor array 312 in this illustrative example. Filter 310 is configured to separate electromagnetic radiation in response 228 into number of wavelengths 230. In these illustrative examples, filter 310 takes the form of interference filter 314.

Each of the wavelengths in number of wavelengths 230 separated by filter 310 is sent to a sensor in sensor array 312 in these illustrative examples. As a result, sensor array 312 generates data from number of wavelengths 230 from response 228 from a particular location in number of locations 244.

In these illustrative examples, director system 304 is a hardware system that is configured to direct response 228 onto filter 310. Director system 304 may cause response 228 to be scanned across filter 310. As response 228 is scanned across filter 310, number of wavelengths 230 is separated out in response 228 by filter 310.

Director system 304 may be comprised of components such as mirror system 318, opening 320, and other suitable types of components. Mirror system 318 may be moveable to cause response 228 to scan across filter 310. Opening 320 may be, for example, an opening in platform 308 that allows a portion of response 228 that corresponds to a location in number of locations 244 to be directed onto filter 310.

Visible light sensor system 302 is configured to generate image data of surface 212 of composite workpiece 206 in these illustrative examples. Visible light sensor system 302 may be implemented using any type of visible light camera or components from a visible light camera.

Projector 306 is configured to project images. In these illustrative examples, projector 306 may be configured to project image 234 onto surface 212 of composite workpiece 206.

Controller 307 is a hardware device and may include software. Controller 307 is configured to control the operation of at least one of spectral sensor system 300, visible light sensor system 302, director system 304, and projector 306. Controller 307 also may be configured to process some of data 232 generated by imaging system 216 prior to data 232 being sent to analyzer 222. Controller 307 may be a processor unit, an integrated circuit system, a computer, or some other suitable hardware device. For example, controller 307 may pre-process data 232 to remove noise, add timestamps, and perform other operations on data 232 prior to sending data 232 to analyzer 222.

Figure 4:
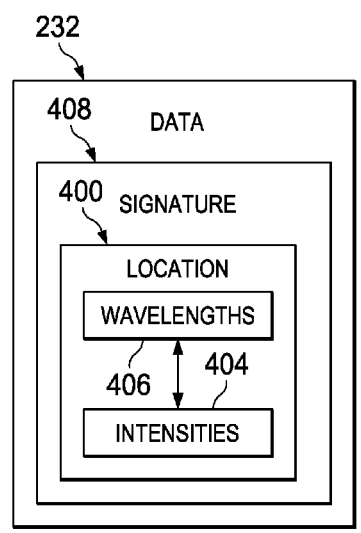
FIG. 4 is an illustration of a block diagram of data in accordance with an illustrative embodiment.

Turning now to FIG. 4, an illustration of a block diagram of data is depicted in accordance with an illustrative embodiment. In this figure, examples of information that may be present in data 232 in FIG. 2 are illustrated. In this illustrative example, data 232 represents data for location 400. Location 400 is an example of a location within number of locations 244 in FIG. 2.

Location 400 is a location identified on surface 212 of composite workpiece 206. Location 400 may be described in terms of coordinates. For example, a coordinate system for the workpiece may be used to identify location 400. Of course, any suitable coordinate system may be used to identify location 400. Location 400 may be identified in a number of different ways. For example, location 400 may be identified using a model of composite structure 246. In particular, the model may be a model of the layups for number of composite layers 208. This model may include a coordinate system. This coordinate system may be used by analyzer 222 to control imaging system 216 in selecting location 400. In these illustrative examples, the model may be a computer-aided design model of composite structure 246.

In this illustrative example, location 400 has intensities 404 for wavelengths 406. In other words, each wavelength in wavelengths 406 has an intensity in intensities 404.

In these illustrative examples, an intensity in intensities 404 may be measured as lux, which is luminous flux per unit area.

Wavelengths 406 are a range of wavelengths that are continuous in these illustrative examples. The wavelengths in wavelengths 406 may vary depending on the particular implementation. For example, wavelengths 406 may be from about 500 nanometers to about 3,600 nanometers. Of course, other wavelengths may be used and the wavelengths may even be discontinuous in some illustrative examples.

In these illustrative examples, intensities 404 for wavelengths 406 at location 400 form signature 408 for location 400. Signature 408 may be compared to known signatures in signature database 240 to determine whether a contaminant is present at location 400 in these illustrative examples.

The illustration of inspection environment 200 and the different components in FIGS. 2-4 are not meant to imply physical or architectural limitations to the manner in which inspection environment 200 may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, spectral sensor system 300, visible light sensor system 302, and projector 306 may be associated with different platforms rather than the same platform. In some illustrative examples, controller 307 may be located in computer system 238 at a location remote to platform 308.

In another illustrative example, imaging system 216 may include other components in addition to the ones illustrated in FIG. 3. For example, imaging system 216 also may include a lens system. The lens system may be configured to focus light that may be received in response 228.

In another illustrative example, composite workpiece 206 may be processed to form composite structure 246 in other forms other than a composite aircraft part for an aircraft. For example, without limitations, composite structure 246 may be a part for a platform, such as a mobile platform, a stationary platform, a land-based structure, an aquatic-based structure, and a space-based structure. More specifically, the platform may be a surface ship, a tank, a personnel carrier, a train, a spacecraft, a space station, a satellite, a submarine, an automobile, a power plant, a bridge, a dam, a manufacturing facility, a building, and other suitable objects.

Figure 5:
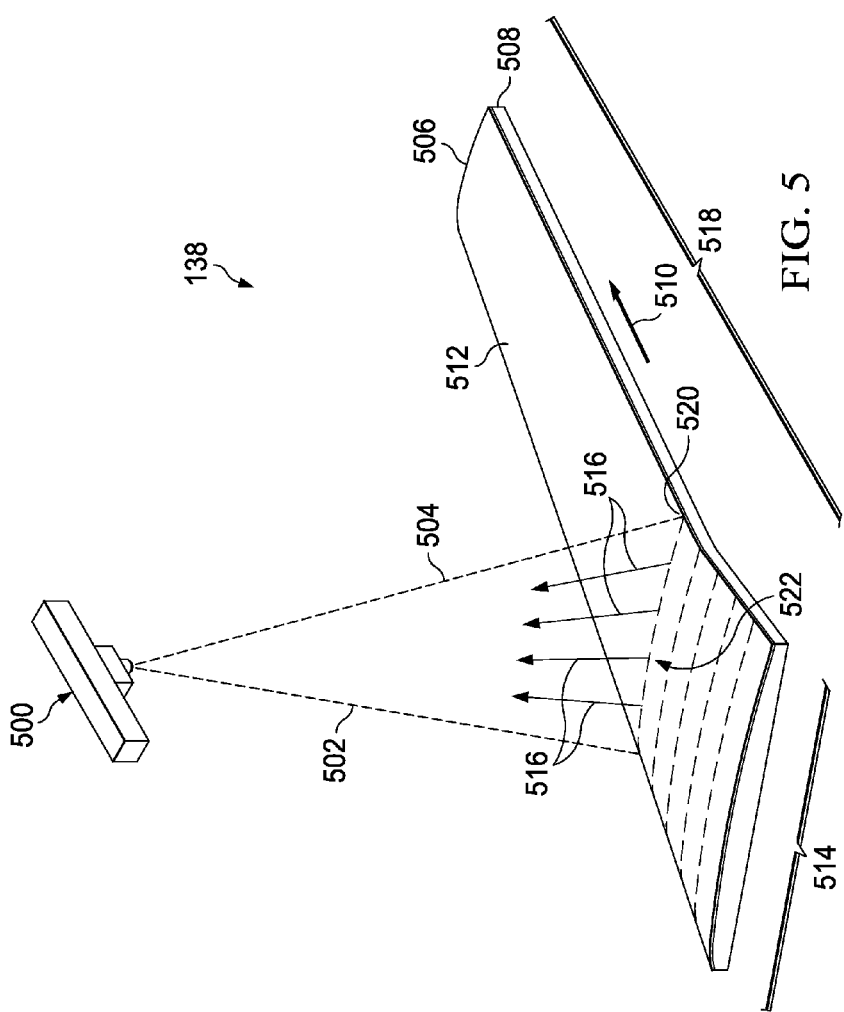
FIG. 5 is an illustration of an imaging system in accordance with an illustrative embodiment.

Turning now to FIG. 5, an illustration of an imaging system is depicted in accordance with an illustrative embodiment. As depicted, imaging system 500 is an example of a physical implementation of imaging system 216 shown in block form in FIG. 2 and FIG. 3.

In this depicted example, imaging system 500 may direct electromagnetic radiation 502 in the form of coherent light 504 to scan composite workpiece 506 laid up on tool 508. In particular, coherent light 504 may be configured to be scanned in the direction of arrow 510 across surface 512 of composite workpiece 506. In this depicted example, composite workpiece 506 is a composite workpiece for a wing of an aircraft.

In this illustrative example, coherent light 504 may cover width 514 of composite workpiece 506 while moving in the direction of arrow 510. In response to coherent light 504, response 516 is returned to imaging system 500. As depicted, response 516 is a response for position 520 along length 518 of composite workpiece 506. Response 516 is the response that may be separated into wavelengths.

More specifically, a plurality of locations is present along width 514 for each position along length 518 of composite workpiece 506. For example, position 520 has plurality of locations 522. Each location in plurality of locations 522 may reflect coherent light 504 in a manner that generates a portion of response 516. The portion of response 516 corresponding to a position in plurality of locations 522 is separated into one or more wavelengths to generate data for that particular location in plurality of locations 522 at position 520.

In these illustrative examples, coherent light 504 may be steered by imaging system 500 while imaging system 500 is stationary. In other illustrative examples, imaging system 500 may move in the direction of arrow 510. In some illustrative examples, a combination of the two may occur to cause coherent light 504 to scan composite workpiece 506 in the direction of arrow 510 along length 518 of composite workpiece 506.

Figure 6:
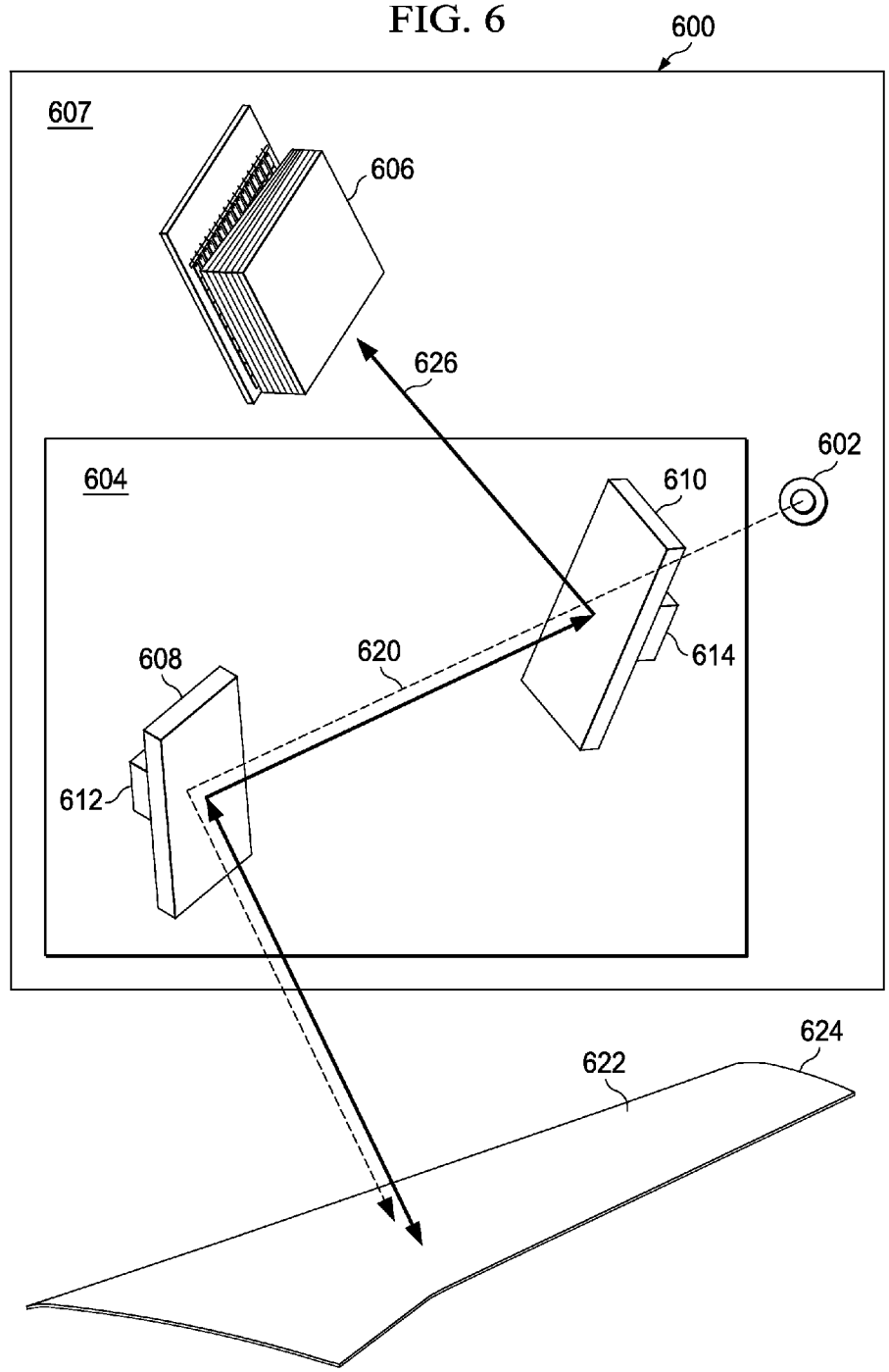
FIG. 6 is an illustration of an imaging system in accordance with an illustrative embodiment.

Referring now to FIG. 6, an illustration of an imaging system is depicted in accordance with an illustrative embodiment. Imaging system 600 is an example of one implementation for imaging system 216 shown in block form in FIG. 2 and FIG. 3. Imaging system 600 comprises electromagnetic radiation source 602, director system 604, spectral sensor system 606, and housing 607.

Electromagnetic radiation source 602 is configured to generate electromagnetic radiation in the form of coherent light. Electromagnetic radiation source 602 takes the form of a laser system in this particular example.

As depicted, electromagnetic radiation source 602 generates beam of coherent light 620. Beam of coherent light 620 passes through scanning mirror 610 and is reflected off of scanning mirror 608 toward surface 622 of composite workpiece 624.

Scanning mirror 610 is reflective in one direction such that beam of coherent light 620 may pass through scanning mirror 610. Scanning mirror 610 may be a half silver mirror.

As depicted, scanning mirror 608 is configured to direct electromagnetic radiation from electromagnetic radiation source 602 toward a composite workpiece. However, alternative embodiments may not include scanning mirror 608. In alternative embodiments, electromagnetic radiation source 602 may be directed at a composite workpiece. In such alternative embodiments, electromagnetic radiation source 602 may or may not be located within housing 607 of imaging system 600. Further, additional optics or directing means may be present in alternative embodiments to control electromagnetic radiation directed to a composite workpiece from electromagnetic radiation source 602.

Director system 604 is an example of an implementation for director system 304 shown in block form in FIG. 3. Director system 604 directs beam of coherent light 620 from electromagnetic radiation source 602 to surface 622 of composite workpiece 624. Director system 604 also directs response 626 to beam of coherent light 620 from surface 622 of composite workpiece 624 to spectral sensor system 606.

As depicted, director system 604 comprises scanning mirror 608 and scanning mirror 610. However, in alternative embodiments, director system 604 may comprise more or less components. Further, in alternative embodiments, director system 604 may include different directing components such as a rotating polygon, a rotating mirror monogon, or a prismatic polygon.

As depicted, scanning mirror 608 is connected to driving mechanism 612. Driving mechanism 612 controls the position of scanning mirror 608. Driving mechanism 612 may be implemented using a motor or other device that is configured to control the position of scanning mirror 608.

The position of scanning mirror 608 controls the direction of beam of coherent light 620 toward composite workpiece 624. As a result, movement of scanning mirror 608 may cause beam of coherent light 620 to be directed toward different locations on surface 622 of composite workpiece 624. Thus, scanning mirror 608 may be moved by driving mechanism 612 such that beam of coherent light 620 scans surface 622 of composite workpiece 624.

Likewise, the position of scanning mirror 610 directs response 626 received from the composite workpiece 624. In these illustrative examples, response 626 is directed by the position of scanning mirror 610 to different portions of spectral sensor system 606 within imaging system 600.

Scanning mirror 610 is connected to driving mechanism 614. Driving mechanism 614 controls the position of scanning mirror 610. Like scanning mirror 608, the position of scanning mirror 610 directs response 626 to different portions of spectral sensor system 606 in imaging system 600. In particular, response 626 may be directed toward different locations on spectral sensor system 606 to cause the generation of different wavelengths for a particular location on surface 622 of composite workpiece 624. In turn, spectral sensor system 606 separates response 626 into a number of wavelengths. Spectral sensor system 606 then generates data from the number of wavelengths separated from response 626.

In one illustrative example, director system 604 is adjusted to sample from a location on a composite workpiece. Scanning mirror 608 of director system 604 is positioned by driving mechanism 612 to an identified position. The identified position of scanning mirror 608 is calculated to direct beam of coherent light 620 from electromagnetic radiation source 602 to a selected location on surface 622 of composite workpiece 624. Scanning mirror 610 of director system 604 is positioned by driving mechanism 614 to an identified position. The identified position of scanning mirror 610 is calculated to direct a response received from scanning mirror 608 to spectral sensor system 606.

After director system 604 is adjusted, electromagnetic radiation source 602 transmits beam of coherent light 620 through scanning mirror 610. Beam of coherent light 620 is directed by scanning mirror 608 to the location to be sampled on composite workpiece 624.

Response 626 to beam of coherent light 620 from surface 622 of composite workpiece 624 is directed by scanning mirror 608 to scanning mirror 610. Scanning mirror 610 directs response 626 to spectral sensor system 606. In this illustrative example, response 626 may be scanned across spectral sensor system 606 through movement of scanning mirror 610 to different positions while receiving response 626.

Spectral sensor system 606 receives the response, separates the response into a number wavelengths, and generates data. Imaging system 600 may then transmit data to an analyzer, such as analyzer 222 of FIG. 2.

As depicted, imaging system 600 of FIG. 6 changes the location of a composite workpiece to be sampled by adjusting director system 604. Accordingly, in this illustrative example, after a first location of composite workpiece 624 is sampled, a second location of the composite workpiece is identified. Scanning mirror 608 is adjusted by driving mechanism 612 to a second position. The second position is calculated to direct beam of coherent light 620 from electromagnetic radiation source 602 to the second location on surface 622 of composite workpiece 624. Likewise, scanning mirror 610 is adjusted to move to different positions by driving mechanism 614 to receive a response from scanning mirror 608 in the second position. In this manner, response 626 to beam of coherent light 620 directed to the second location may be scanned across spectral sensor system 606. In this illustrative example, different locations on surface 622 of composite workpiece 624 are sampled by the adjusting director system 604. In this illustrative example, imaging system 600 remains stationary.

However, changing the location of the composite workpiece to be sampled may be accomplished in other ways. For example, in other illustrative examples, rather than adjusting director system 604, imaging system 600 may be moved. Alternatively, rather than adjusting director system 604 or moving imaging system 600, composite workpiece 624 may be moved in relation to imaging system 600. In illustrative examples in which imaging system 600 or composite workpiece 624 are moved in relation to each other, director system 604 need not be comprised of moveable components.

Figure 7:
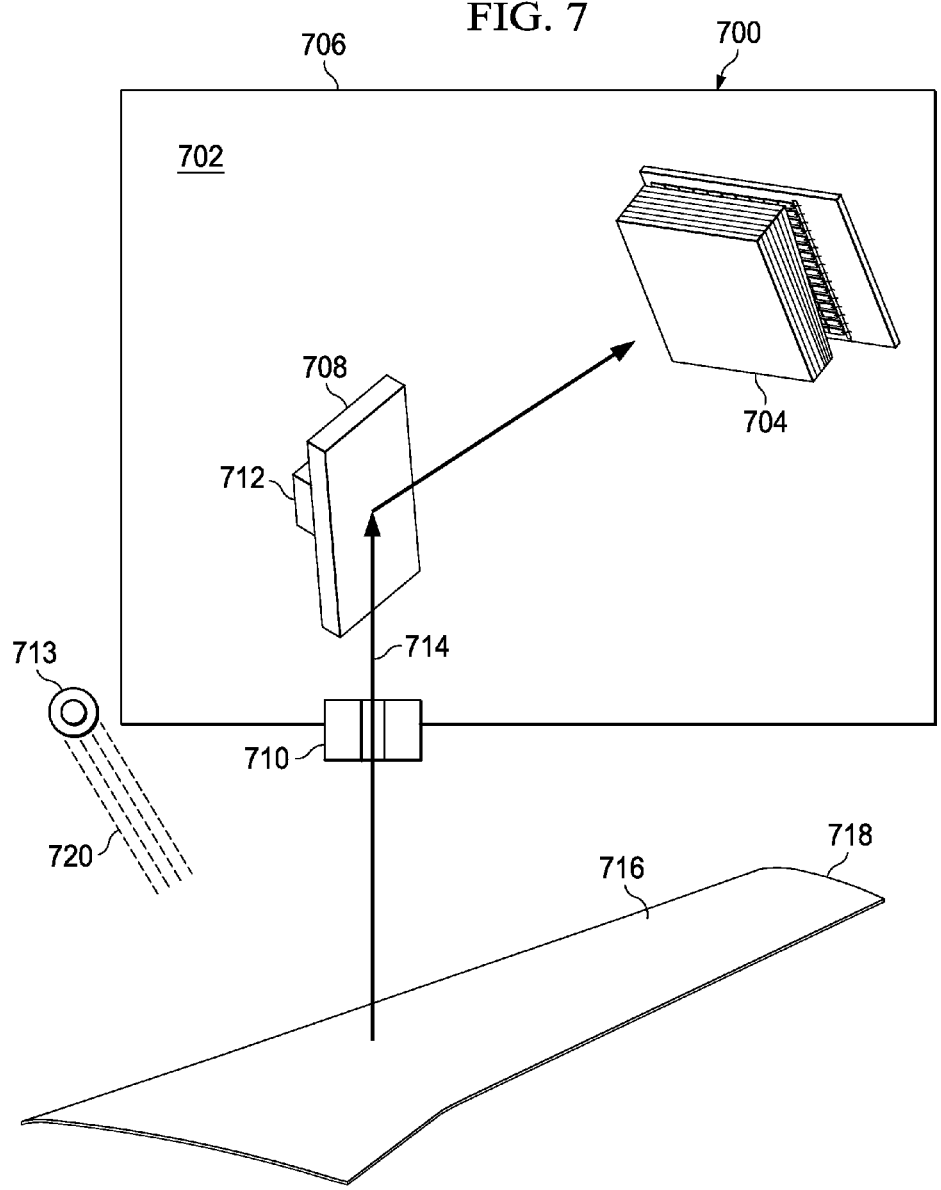
FIG. 7 is an illustration of an imaging system in accordance with an illustrative embodiment.

Turning now to FIG. 7, an illustration of an imaging system is depicted in accordance with an illustrative embodiment. Imaging system 700 is an example of one implementation for imaging system 216 shown in block form in FIG. 2 and FIG. 3. Imaging system 700 comprises director system 702, spectral sensor system 704, and housing 706.

In this illustrative example, spectral sensor system 704 is located inside of housing 706. Director system 702 is comprised of scanning mirror 708 and opening 710. Scanning mirror 708 may be moved to different positions by driving mechanism 712.

As depicted, imaging system 700 does not include electromagnetic radiation source 713 within housing 706. Instead, electromagnetic radiation source 713 may be elsewhere in imaging system 700 or part of another system.

In this depicted example, response 714 is received through opening 710 in housing 706. Response 714 is directed toward spectral sensor system 704 by scanning mirror 708.

In this illustrative example, response 714 may be directed toward different locations on spectral sensor system 704 through movement of scanning mirror 708 to different positions. Response 714 from a particular location on surface 716 of composite workpiece 718 is a response to electromagnetic radiation 720 being directed to surface 716 of composite workpiece 718. Response 714 is selected through movement of housing 706. In particular, the movement of opening 710 over different locations on surface 716 of composite workpiece 718 is used to select the location for which response 714 is received in these illustrative examples.

Figure 8:
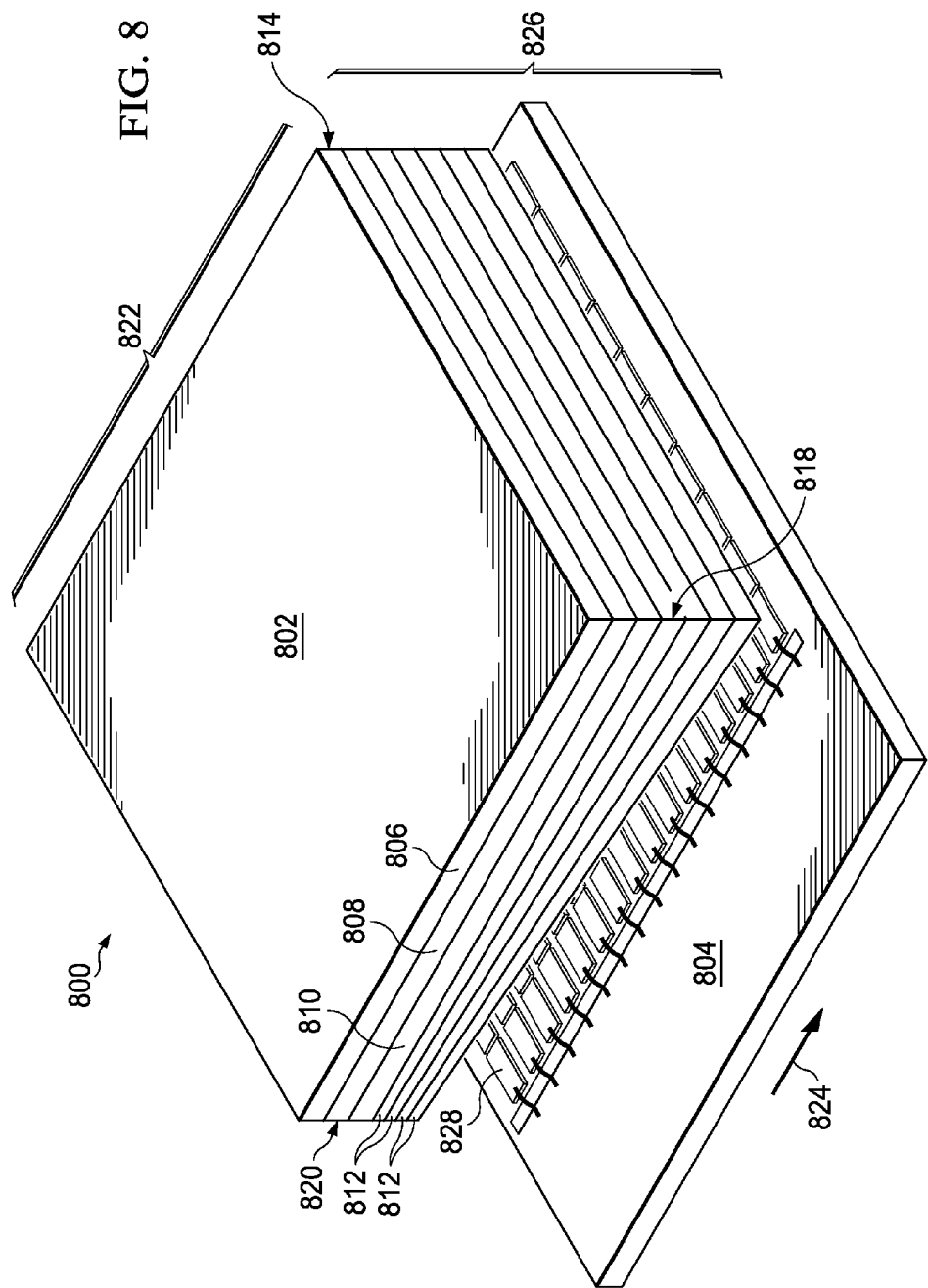
FIG. 8 is an illustration of a spectral sensor system in accordance with an illustrative embodiment.

Turning now to FIG. 8, an illustration of a spectral sensor system is depicted in accordance with an illustrative embodiment. In this illustrative example, spectral sensor system 800 is an example of one physical implementation for spectral sensor system 300 shown in block form in FIG. 3. In this illustrative example, spectral sensor system 800 includes filter 802 and sensor array 804. Filter 802 takes the form of a wedge filter in these illustrative examples. In one illustrative example, filter 802 may have a range of wavelengths from about 400 nanometers to about 3,600 nanometers.

Filter 802 includes blocking filter 806, substrate 808, and spectral disperser 810. As depicted, substrate 808 is formed on spectral disperser 810. Blocking filter 806 is formed on substrate 808.

Blocking filter 806 in filter 802 is configured to reduce out of band electromagnetic radiation that passes through filter 802. In this illustrative example, blocking filter 806 may reduce electromagnetic radiation that passes through blocking filter 806 that has a wavelength that is outside of a range from about 400 nanometers to about 1,000 nanometers or a wavelength that is outside of a range from about 500 nanometers to about 3,600 nanometers. Of course, other ranges may be used depending on the particular implementation.

In these illustrative examples, blocking filter 806 is comprised of material that may be selected to reduce radiation for particular wavelengths in a spectral region. In other illustrative examples, the material used to form blocking filter 806 may be selected to reduce substantially all of the radiation that is out of band for blocking filter 806. In these illustrative examples, electromagnetic radiation is out of band for blocking filter 806 when the electromagnetic radiation has a wavelength that is from about 400 nanometers to about 1,000 nanometers.

Substrate 808 may be comprised of material that is selected to be substantially transparent for electromagnetic radiation having a wavelength or wavelengths of interest. In other words, substrate 808 may allow wavelengths of interest to pass while other wavelengths that are not desirable are blocked from passing through substrate 808. In this illustrative example, wavelengths of interest are wavelengths from about 400 nanometers to about 1,000 nanometers.

Spectral disperser 810 is comprised of layers 812. Layers 812 include layers having different refractive indexes. In these illustrative examples, layers 812 are tapered in thickness to create wedge shape 814. In other words, layers 812 are thicker at edge 818 than at edge 820 of spectral disperser 810. The materials and thickness of these layers are selected to provide the range of frequencies that may be separated by filter 802.

In these illustrative examples, length 822 of filter 802 defines the range of frequencies that may be passed by filter 802. In other words, the wavelength passed through filter 802 is dependent upon the location along length 822 in which electromagnetic radiation passes into filter 802. In other words, length 822 is a spectral dimension for filter 802.

In other words, the wavelength passed by filter 802 increases in the direction of arrow 824. Thus, edge 820 provides a shortest wavelength that may be passed by filter 802 while edge 818 provides a longest wavelength that may be passed by filter 802.

Length 826 is a spatial dimension for filter 802. Locations along length 826 correspond to locations on a surface of a composite workpiece in these illustrative examples. In one illustrative example, locations along length 826 may correspond to plurality of locations 522 along width 514 of composite workpiece 506 in FIG. 5.

Sensor array 804 is comprised of sensors 828. In these illustrative examples, sensors 828 are arranged in rows and columns. The size of sensors 828 may affect the spectral resolution and spatial resolution for spectral sensor system 800. In these illustrative examples, sensors 828 are configured to generate signals in response to detecting electromagnetic radiation. These signals may represent amplitude, intensity, or other parameters depending on the particular implementation. These signals form some or all of data 232 in FIG. 2.

Sensor array 804 may be implemented using different types of sensors. For example, sensors 828 in sensor array 804 may be comprised of digital-charged-coupled-devices, complimentary metal oxide semiconductor devices, indium antimonide (InSb) semiconductor devices, mercury cadmium telluride (HgCdTe) semiconductor devices, or any other type of sensors suitable for detecting electromagnetic radiation.

The illustrations of imaging system 500 in FIG. 5, imaging system 600 in FIG. 6, and imaging system 700 in FIG. 7 are not meant to limit the manner in which imaging system 216 may be implemented. For example, other imaging systems also may include a visible light sensor system, a projector, or both in addition to the components illustrated for imaging system 500, imaging system 600, and imaging system 700. As another illustrative example, multiple sources of coherent light may be present. In other words, one or more additional sources of coherent light may be present in addition to the source emitting coherent light 504 in imaging system 500.

In another illustrative example, other forms of electromagnetic radiation may be used in addition to or in place of coherent light. For example, electromagnetic radiation may be non-coherent light from arc lamp or a light emitting diode.

Further, the illustration of spectral sensor system 800 in FIG. 8 is not meant to limit the manner in which spectral sensor system 800 may be implemented in imaging system 600 and imaging system 700. For example, other types of structures may be used in place of or in addition to the wedge shaped filter used for filter 802. For example, other structures may be selected from at least one of an optical prism, a holographic grating, a conventional grating, and other suitable types of structures.

Figure 9:
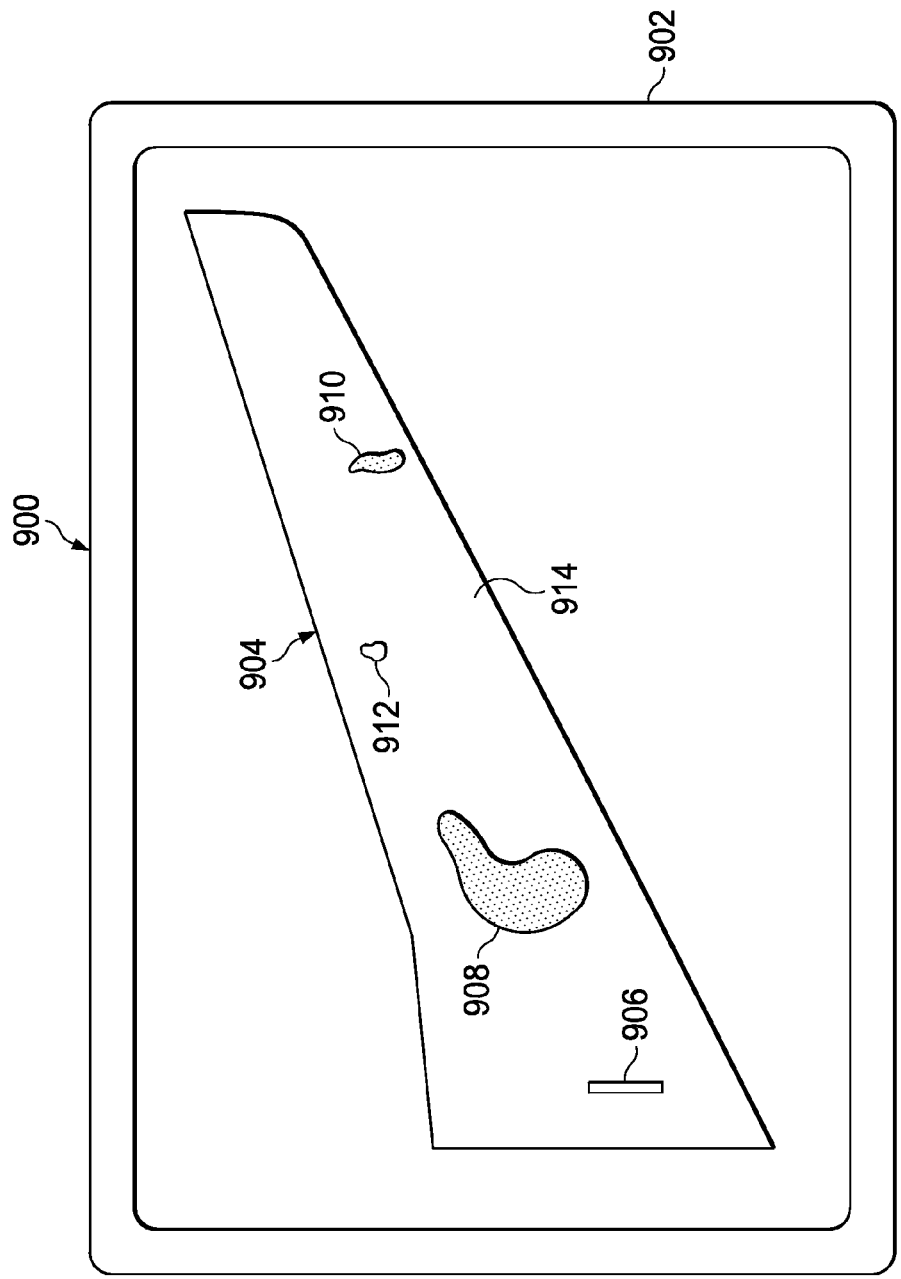
FIG. 9 is an illustration of a two-dimensional image with graphical indicators in accordance with an illustrative embodiment.

With reference next to FIG. 9, an illustration of a two-dimensional image with graphical indicators is depicted in accordance with an illustrative embodiment. As depicted, image 900 is an example of an implementation of image 234 shown in block form in FIG. 2.

In this illustrative example, image 900 is two-dimensional image 902. As depicted, two-dimensional image 902 is an image of composite workpiece 904. Composite workpiece 904 is a composite workpiece for a wing of an aircraft in these illustrative examples.

In this illustrative example, two-dimensional image 902 includes graphical indicators 906, 908, 910, and 912. These graphical indicators are a set of graphical indicators identifying a set of contaminants on surface 914 of composite workpiece 904.

In this illustrative example, graphical indicator 906 indicates a presence of an unknown contaminant on surface 914 of composite workpiece 904. Graphical indicator 908 and graphical indicator 910 indicate a presence of water on surface 914 of composite workpiece 904. Graphical indicator 912 indicates a presence of a plastic particle on surface 914 of composite workpiece 904.

With two-dimensional image 902, an operator may identify contaminants present on surface 914 of composite workpiece 904. In this manner, these contaminants may be taken into account prior to finishing layup of layers of composite material on composite workpiece 904 and curing composite workpiece 904. For example, contaminants may be removed from surface 914. In other illustrative examples, one or more layers may be replaced in composite workpiece 904.

The different components shown in FIG. 1 and FIGS. 4-9 may be combined with components in FIGS. 2-4, used with components in FIGS. 2-4, or a combination of the two. Additionally, some of the components in FIG. 1 and FIGS. 4-9 may be illustrative examples of how components shown in block form in FIGS. 2-4 can be implemented as physical structures.

Figure 10:
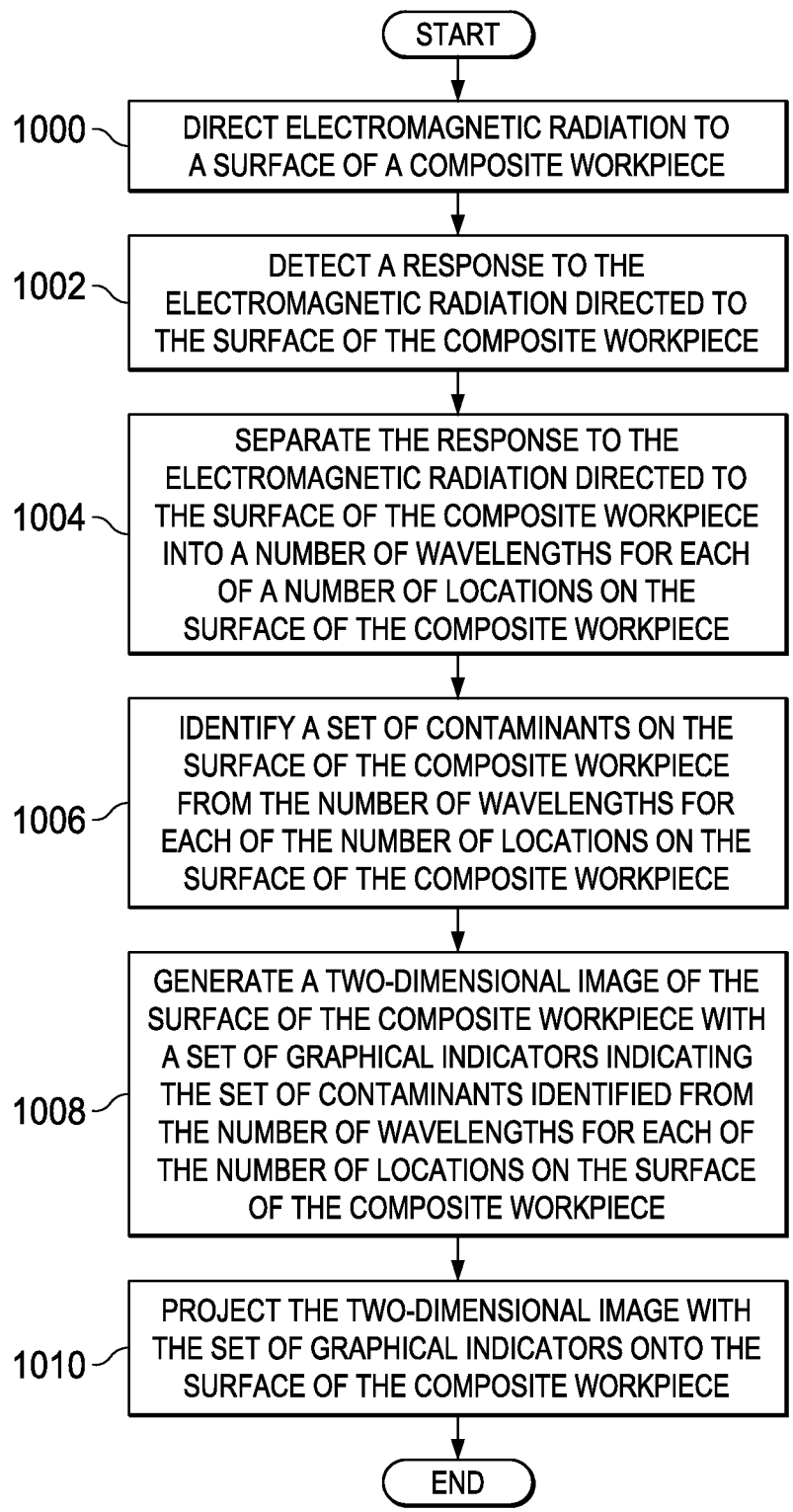
FIG. 10 is an illustration of a flowchart of a process for inspecting a composite workpiece in accordance with an illustrative embodiment.

With reference now to FIG. 10, an illustration of a flowchart of a process for inspecting a composite workpiece is depicted in accordance with an illustrative embodiment. In this depicted example, the process illustrated in FIG. 10 may be implemented in inspection environment 200 in FIG. 2 for use in manufacturing environment 100 in FIG. 1. In these illustrative examples, the process may be used to inspect workpieces such as composite workpiece 206 in FIG. 2. This process is performed prior to the composite workpiece being cured or particular layers on the composite workpiece being cured.

The process begins by directing electromagnetic radiation to a surface of a composite workpiece (operation 1000). The electromagnetic radiation may originate from electromagnetic radiation source 218 in FIG. 2. The process then detects a response to the electromagnetic radiation directed to the surface of the composite workpiece (operation 1002). The response may be detected and processed in the subsequent operations in this figure by inspection system 202 in FIG. 2. Next, the response to the electromagnetic radiation directed to the surface of the composite workpiece is separated into a number of wavelengths for each of a number of locations on the surface of the composite workpiece (operation 1004). The electromagnetic radiation may be separated by imaging system 216 in inspection system 202. The response may be for more than one location. In these illustrative examples, the response may be along a line or some other area. In one illustrative example, the response may be for plurality of locations 522 at position 520 along length 518 of composite workpiece 506 in FIG. 5.

Next, the process identifies a set of contaminants on the surface of the composite workpiece from the number of wavelengths for each of the number of locations on the surface of the composite workpiece (operation 1006). The identification of contaminants in operation 1006 may be performed by analyzer 222 in inspection system 202. In these illustrative examples, the set of contaminants may be zero contaminants in some cases if none are detected.

A two-dimensional image of the surface of the composite workpiece with a set of graphical indicators indicating the set of contaminants identified from the number of wavelengths for each of the number of locations on the surface of the composite workpiece is generated (operation 1008). The two-dimensional image may be generated by analyzer 222. In this illustrative example, each of the contaminants is identified using a graphical indicator. If no contaminants are present, then the set of graphical indicators is an empty set. In these illustrative examples, the two-dimensional image may be generated using data from the wavelengths.

For example, for places where contaminants are not present, the image may use a particular graphical indicator to indicate an absence of contaminants. In other illustrative examples, the graphical indicators may be placed in a visible light image generated of the surface of the composite workpiece. The visible light image may also be generated by imaging system 216 in inspection system 202 in FIG. 2.

The process then projects the two-dimensional image with the set of graphical indicators onto the surface of the composite workpiece (operation 1010) with the process terminating thereafter. The projection of the two-dimensional image onto the surface of the workpiece may be performed using imaging system 216 under the control of analyzer 222.

Figure 11:
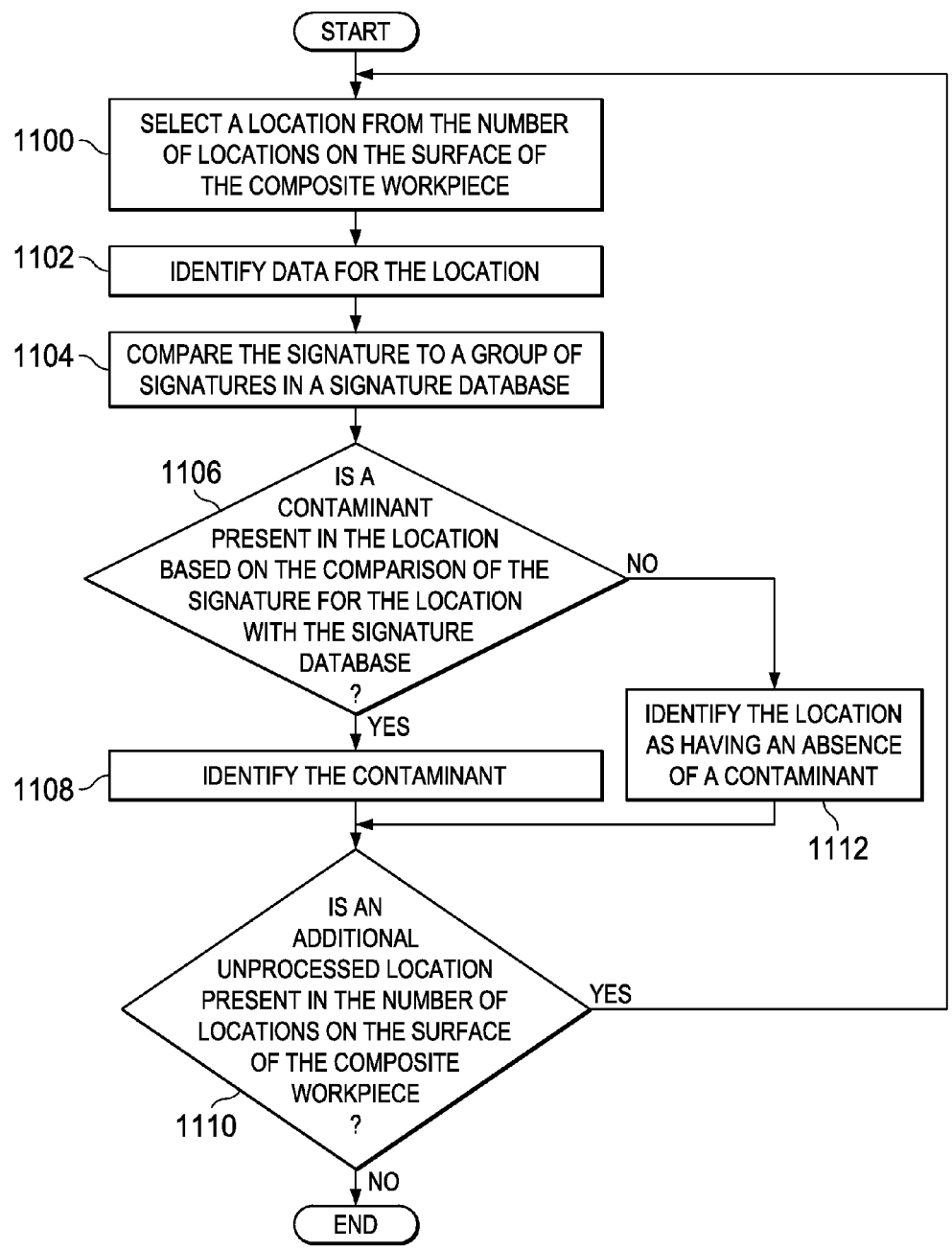
FIG. 11 is an illustration of a flowchart of a process for identifying a set of contaminants from a number of wavelengths in accordance with an illustrative embodiment.

Turning now to FIG. 11, an illustration of a flowchart of a process for identifying a set of contaminants from a number of wavelengths is depicted in accordance with an illustrative embodiment. The process illustrated in FIG. 11 is an example of one implementation of operation 1006 in FIG. 10.

The process begins by selecting a location from the number of locations on the surface of the composite workpiece (operation 1100). For example, the location may be a location within plurality of locations 522 for composite workpiece 506 in FIG. 5. In other illustrative examples, the number of locations may be all of the locations across width 514 for all positions along length 518 of composite workpiece 506.

Data for the location is identified (operation 1102). This data is data generated from a number of wavelengths for the selected locations. The data may include, for example, a wavelength and a value for the wavelength. This value may be an intensity, an amplitude, or some other suitable value. The data for the location is a signature for that location in these illustrative examples.

The process then compares the signature to a group of signatures in a signature database (operation 1104). The signature database may be, for example, signature database 240 in FIG. 2. The signature database includes signatures for known contaminants. Further, the database also may include signatures for known composite materials that should be present in the composite workpiece.

A determination is then made as to whether a contaminant is present in the location based on the comparison of the signature for the location with the signature database (operation 1106). If a contaminant is present, the process then identifies the contaminant (operation 1108). This identification may be based on identifying the contaminant as being one in the signature database. In some cases, if the contaminant does not match a signature for known contaminants in the signature database and also does not match a signature for composite materials that should be present, the contaminant is identified as an unknown contaminant.

Thereafter, a determination is made as to whether an additional unprocessed location is present in the number of locations on the surface of the composite workpiece (operation 1110). If an additional unprocessed location is present, the process returns to operation 1100. Otherwise, the process terminates.

With reference again to operation 1106, if a contaminant is not present, the location is identified as having an absence of a contaminant (operation 1112) with the process then proceeding to operation 1110 as described above. In operation 1112, the identification may include an identification of the material that is present at the location. In this case, the material is one that is expected to be present for the composite workpiece.

Figure 12:
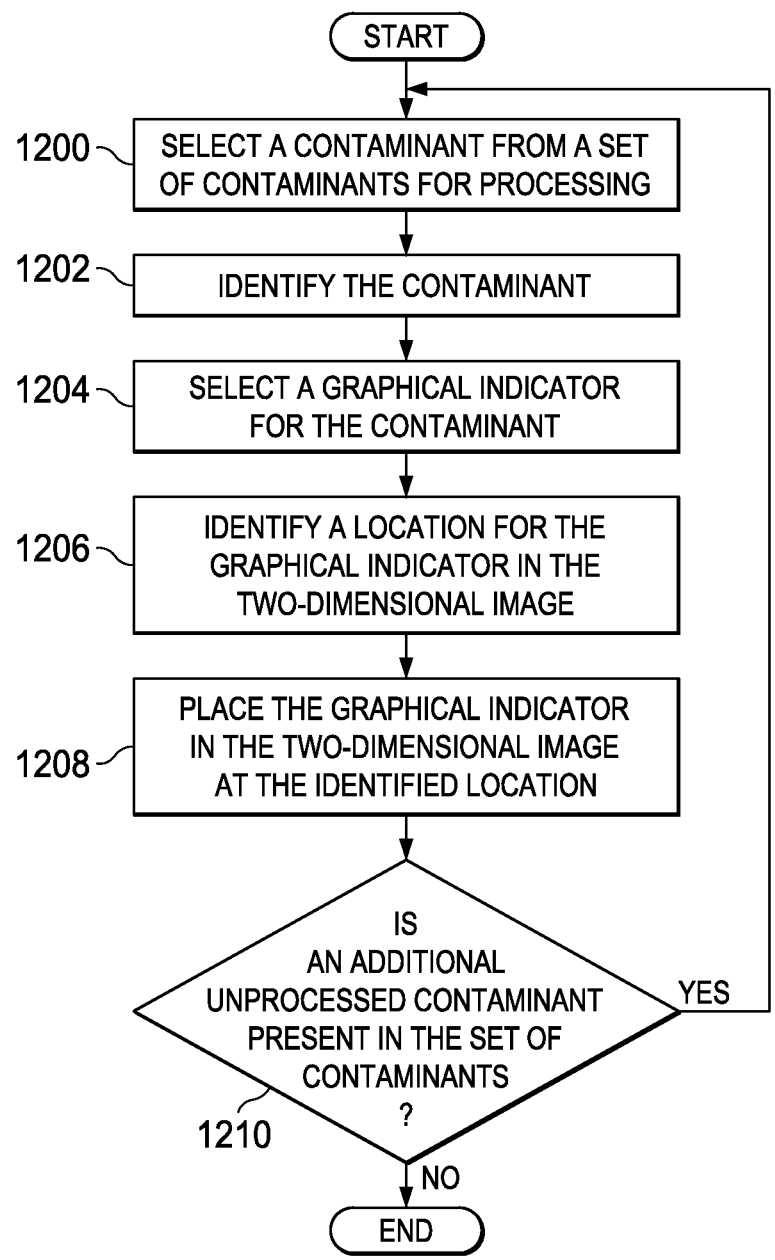
FIG. 12 is an illustration of a flowchart of a process for generating a two-dimensional image of a surface of a composite workpiece with a set of graphical indicators indicating a set of contaminants in accordance with an illustrative embodiment.

Turning now to FIG. 12, an illustration of a flowchart of a process for generating a two-dimensional image of a surface of a composite workpiece with a set of graphical indicators indicating a set of contaminants is depicted in accordance with an illustrative embodiment. The process illustrated in FIG. 12 is an example of one implementation of operation 1008 in FIG. 10.

The process begins by selecting a contaminant from a set of contaminants for processing (operation 1200). The process identifies the contaminant (operation 1202). The identification is one generated in operation 1108 in FIG. 11.

Based on the identification of the contaminant, the process selects a graphical indicator for the contaminant (operation 1204). The graphical indicator may take various forms. For example, the graphical indicator may be selected from at least one of color, an icon, text, cross-hatching, and other suitable types of graphical indicators. The process then identifies a location for the graphical indicator in the two-dimensional image (operation 1206). The location in the two-dimensional image is a location that corresponds to the location of the contaminant on the surface of the workpiece. The process then places the graphical indicator in the two-dimensional image at the identified location (operation 1208).

Next, a determination is made as to whether an additional unprocessed contaminant is present in the set of contaminants identified (operation 1210). If an additional unprocessed contaminant is present for processing, the process returns to operation 1200.

Otherwise, the process terminates with the two-dimensional image being ready for analysis by an operator. The operator may view the image on a display device. In some illustrative examples, the two-dimensional image may be projected onto the surface of the workpiece. The projection of the two-dimensional image is made such that the graphical indicators are located in locations where the contaminants are actually present on the surface of the workpiece. Further, the shape and size of the graphical indicators may be selected such that they have the same size and shape of the contaminants on the surface of the workpiece.

Figure 13:
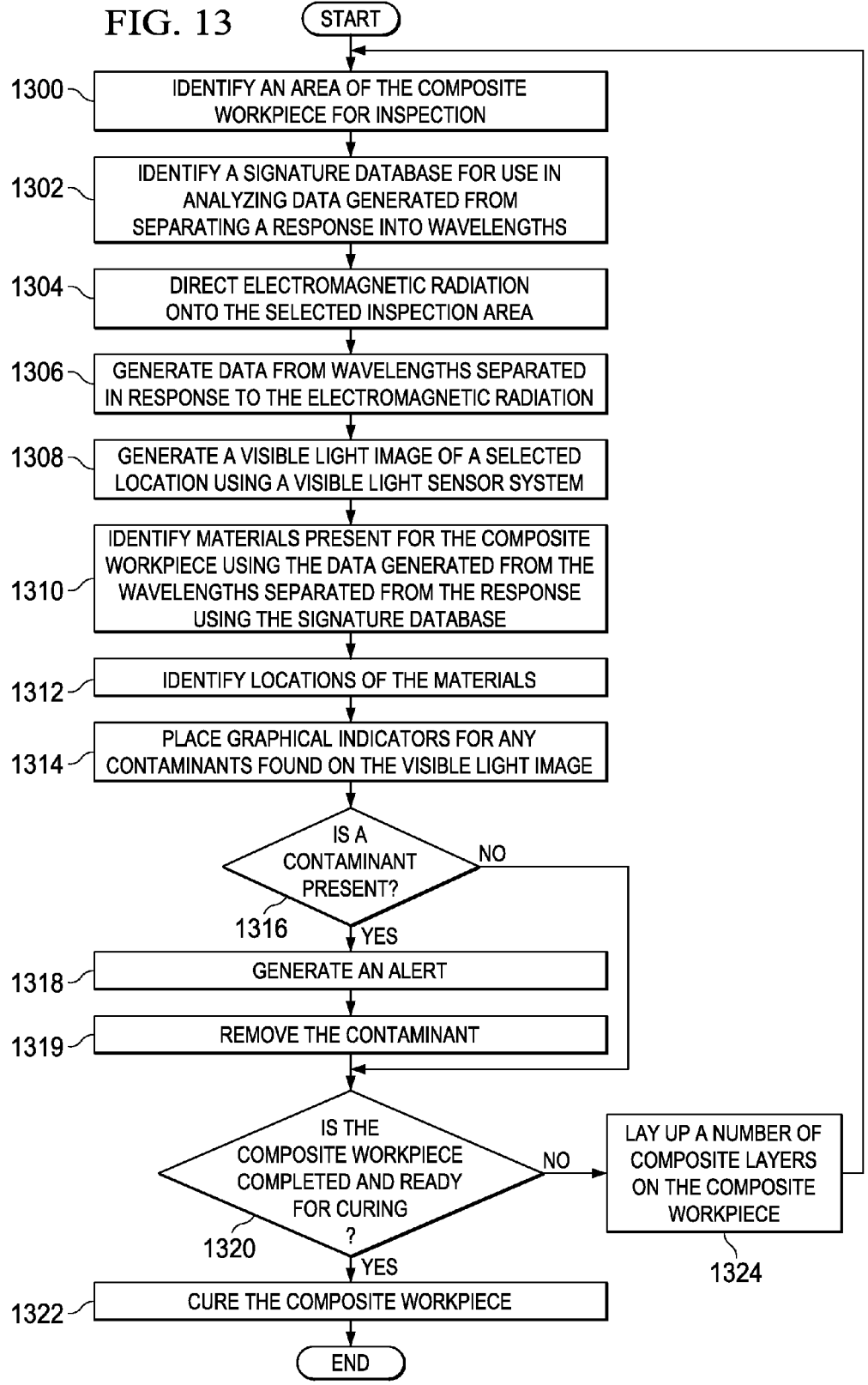
FIG. 13 is an illustration of a flowchart of a process for inspecting a composite workpiece in accordance with an illustrative embodiment.

Turning now to FIG. 13, an illustration of a flowchart of a process for inspecting a composite workpiece is depicted in accordance with an illustrative embodiment. In this illustrative example, the process in FIG. 13 may be implemented in inspection environment 200 in FIG. 2 for use within manufacturing environment 100 in FIG. 1. In particular, the different operations may be implemented in inspection system 202 in FIG. 2.

The process begins by identifying an area of the composite workpiece for inspection (operation 1300). The area may be a portion or all of the composite workpiece depending on the particular implementation.

For example, for reducing time needed for inspections, an area selected may be one that has had an undesired number of inconsistencies during previous manufacturing of the composite structure. This identification may be made from statistical information from manufacturing the same composite structure over time. In other illustrative examples, the area may be selected as one having geometries that are sufficiently complex that inconsistencies may be expected to be higher than desired.

The process then identifies a signature database for use in analyzing data generated from separating a response into wavelengths (operation 1302). The process then directs electromagnetic radiation onto the selected inspection area (operation 1304).

Thereafter, the process generates data from wavelengths separated in response to the electromagnetic radiation (operation 1306). The process generates a visible light image of a selected location using a visible light sensor system (operation 1308).

The process then identifies materials present for the composite workpiece using the data generated from the wavelengths separated from the response using the signature database (operation 1310). Operation 1310 identifies contaminants as well as materials expected to be present for the composite workpiece.

The process then identifies locations of the materials (operation 1312). The locations may be coordinates for the composite workpiece. Of course, any coordinate system may be used. In these illustrative examples, the coordinate system may be a two-dimensional or three-dimensional coordinate system in which an origin is present somewhere on the composite workpiece.

The process then places graphical indicators for any contaminants found on the visible light image (operation 1314). The process then determines whether a contaminant is present (operation 1316). If a contaminant is present, then an alert is generated (operation 1318). Thereafter, the contaminant may be removed (operation 1319). A determination is then made as to whether the composite workpiece is completed and ready for curing (operation 1320). If the composite workpiece is completed, the process then cures the composite workpiece (operation 1322) with the process terminating thereafter.

With reference again to operation 1316, if contaminants are not present, the process also proceeds to operation 1320. With reference again to operation 1320, if the composite workpiece is not completed, then a number of composite layers are laid up on the composite workpiece (operation 1324). The process then returns to operation 1300).

The flowcharts and block diagrams in the different depicted embodiments illustrate the architecture, functionality, and operation of some possible implementations of apparatus and methods in an illustrative embodiment. In this regard, each block in the flowcharts or block diagrams may represent a module, segment, function, and/or a portion of an operation or step. For example, one or more of the blocks may be implemented as program code, in hardware, or a combination of program code and hardware. When implemented in hardware, the hardware may, for example, take the form of integrated circuits that are manufactured or configured to perform one or more operations in the flowcharts or block diagrams.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

Figure 14:
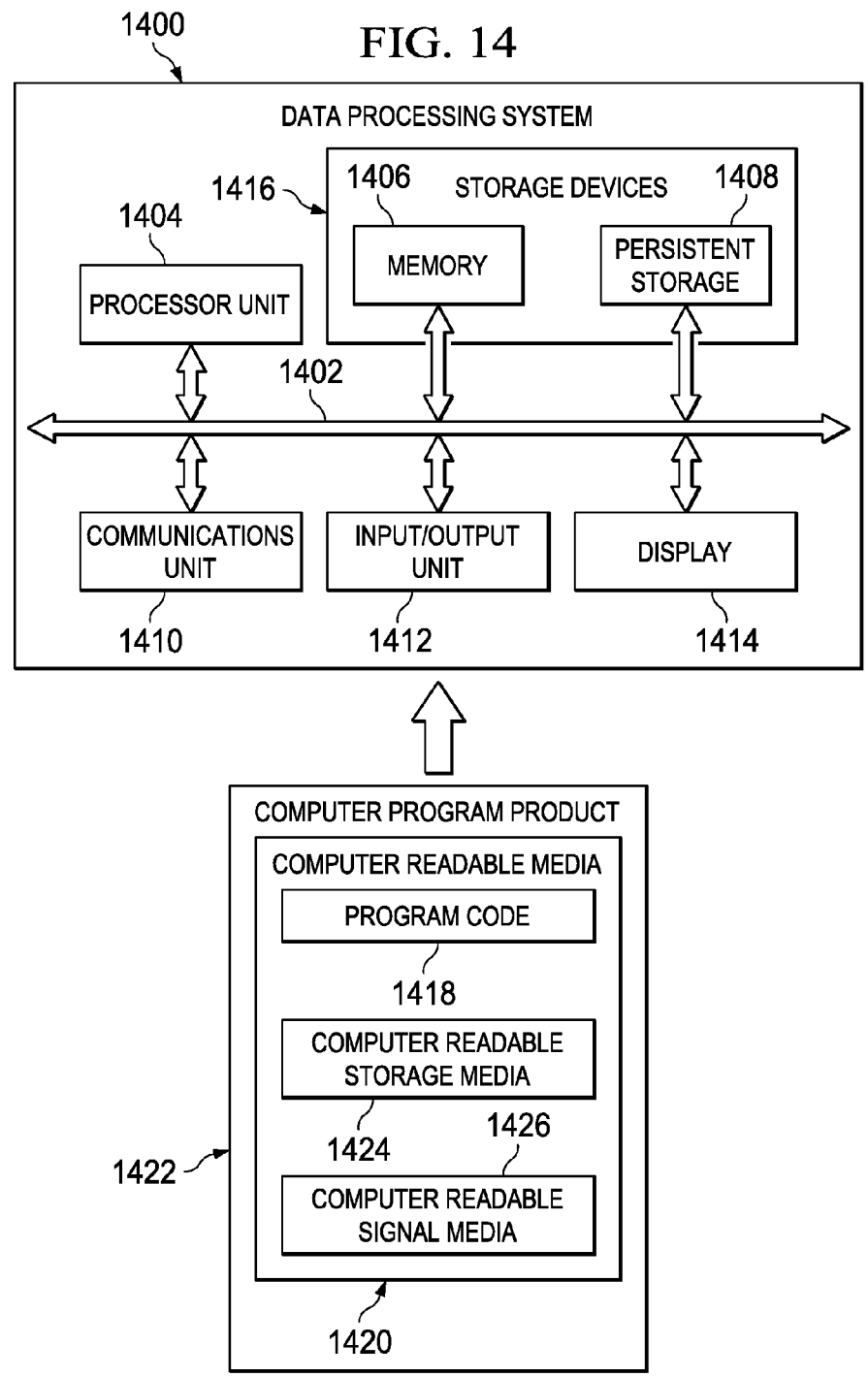
FIG. 14 is an illustration of a data processing system in accordance with an illustrative embodiment.

Turning now to FIG. 14, an illustration of a data processing system is depicted in accordance with an illustrative embodiment. Data processing system 1400 may be used to implement computer system 238 in FIG. 2. In this illustrative example, data processing system 1400 includes communications framework 1402, which provides communications between processor unit 1404, memory 1406, persistent storage 1408, communications unit 1410, input/output (I/O) unit 1412, and display 1414. In this example, communication framework may take the form of a bus system.

Processor unit 1404 serves to execute instructions for software that may be loaded into memory 1406. Processor unit 1404 may be a number of processors, a multi-processor core, or some other type of processor, depending on the particular implementation.

Memory 1406 and persistent storage 1408 are examples of storage devices 1416. A storage device is any piece of hardware that is capable of storing information, such as, for example, without limitation, data, program code in functional form, and/or other suitable information either on a temporary basis and/or a permanent basis. Storage devices 1416 may also be referred to as computer readable storage devices in these illustrative examples. Memory 1406, in these examples, may be, for example, a random access memory or any other suitable volatile or non-volatile storage device. Persistent storage 1408 may take various forms, depending on the particular implementation.

For example, persistent storage 1408 may contain one or more components or devices. For example, persistent storage 1408 may be a hard drive, a flash memory, a rewritable optical disk, a rewritable magnetic tape, or some combination of the above. The media used by persistent storage 1408 also may be removable. For example, a removable hard drive may be used for persistent storage 1408.

Communications unit 1410, in these illustrative examples, provides for communications with other data processing systems or devices. In these illustrative examples, communications unit 1410 is a network interface card.

Input/output unit 1412 allows for input and output of data with other devices that may be connected to data processing system 1400. For example, input/output unit 1412 may provide a connection for user input through a keyboard, a mouse, and/or some other suitable input device. Further, input/output unit 1412 may send output to a printer. Display 1414 provides a mechanism to display information to a user.

Instructions for the operating system, applications, and/or programs may be located in storage devices 1416, which are in communication with processor unit 1404 through communications framework 1402. The processes of the different embodiments may be performed by processor unit 1404 using computer-implemented instructions, which may be located in a memory, such as memory 1406.

These instructions are referred to as program code, computer usable program code, or computer readable program code that may be read and executed by a processor in processor unit 1404. The program code in the different embodiments may be embodied on different physical or computer readable storage media, such as memory 1406 or persistent storage 1408.

Program code 1418 is located in a functional form on computer readable media 1420 that is selectively removable and may be loaded onto or transferred to data processing system 1400 for execution by processor unit 1404. Program code 1418 and computer readable media 1420 form computer program product 1422 in these illustrative examples. In one example, computer readable media 1420 may be computer readable storage media 1424 or computer readable signal media 1426.

In these illustrative examples, computer readable storage media 1424 is a physical or tangible storage device used to store program code 1418 rather than a medium that propagates or transmits program code 1418.

Alternatively, program code 1418 may be transferred to data processing system 1400 using computer readable signal media 1426. Computer readable signal media 1426 may be, for example, a propagated data signal containing program code 1418. For example, computer readable signal media 1426 may be an electromagnetic signal, an optical signal, and/or any other suitable type of signal. These signals may be transmitted over communications links, such as wireless communications links, optical fiber cable, coaxial cable, a wire, and/or any other suitable type of communications link.

The different components illustrated for data processing system 1400 are not meant to provide architectural limitations to the manner in which different embodiments may be implemented. The different illustrative embodiments may be implemented in a data processing system including components in addition to and/or in place of those illustrated for data processing system 1400. Other components shown in FIG. 14 can be varied from the illustrative examples shown. The different embodiments may be implemented using any hardware device or system capable of running program code 1418.

Illustrative embodiments of the disclosure may be described in the context of aircraft manufacturing and service method 1500 as shown in FIG. 15 and aircraft 1600 as shown in FIG. 16. Turning first to FIG. 15, an illustration of an aircraft manufacturing and service method is depicted in accordance with an illustrative embodiment. During pre-production, aircraft manufacturing and service method 1500 may include specification and design 1502 of aircraft 1600 in FIG. 16 and material procurement 1504.

During production, component and subassembly manufacturing 1506 and system integration 1508 of aircraft 1600 in FIG. 16 takes place. Thereafter, aircraft 1600 in FIG. 16 may go through certification and delivery 1510 in order to be placed in service 1512. While in service 1512 by a customer, aircraft 1600 in FIG. 16 is scheduled for routine maintenance and service 1514, which may include modification, reconfiguration, refurbishment, and other maintenance or service.

Each of the processes of aircraft manufacturing and service method 1500 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 16, an illustration of an aircraft is depicted in which an illustrative embodiment may be implemented. In this example, aircraft 1600 is produced by aircraft manufacturing and service method 1500 in FIG. 15 and may include airframe 1602 with plurality of systems 1604 and interior 1606. Examples of systems 1604 include one or more of propulsion system 1608, electrical system 1610, hydraulic system 1612, and environmental system 1614. Any number of other systems may be included. Although an aerospace example is shown, different illustrative embodiments may be applied to other industries, such as the automotive industry.

Apparatus and methods embodied herein may be employed during at least one of the stages of aircraft manufacturing and service method 1500 in FIG. 15.

In the illustrative examples, a method and apparatus may be implemented in inspection environment 200 to inspect composite workpieces formed during components and subassembly manufacturing 1506. As another illustrative example, a method and apparatus in accordance with an illustrative embodiment also may be implemented during maintenance and service 1514 for composite workpieces being processed for forming composite structures used in replacing or upgrading composite structures in aircraft 1600. The use of a number of the different illustrative embodiments may substantially expedite the assembly of and/or reduce the cost of aircraft 1600.

Thus, the illustrative embodiments provide a method and apparatus for inspecting a composite workpiece. Further, the illustrative embodiments also may be used to inspect the surface of a tool on which materials may be laid up to form a composite workpiece. The illustrative embodiments perform inspections to identify contaminants on the surface of a layer of composite material prior to the composite workpiece being cured. In this manner, contaminants or areas containing the contaminants may be removed. As a result, the number of inconsistencies that may be present in a composite structure may be reduced. With the reduction of inconsistencies, the amount of rework or remanufacturing of composite structures also may be reduced.

Further, contaminants may be identified on areas that are not included in the final composite structure. These areas may be, for example, areas of the composite workpiece or layers of composite material for use in forming the composite workpiece. For example, contaminants may be identified on an area of the composite workpiece that will not be used or in an area that will be discarded. In other words, parts of the composite workpiece that will be discarded during manufacturing of a composite structure may not be inspected for contaminants. The presence of contaminants in these types of areas may not be of concern in forming the composite workpiece.

Additionally, the inspection field may be set such that only areas used in the final composite structure may be inspected. Thus, the time required for the inspection and identification of contaminants on a composite workpiece may be reduced.

The different illustrative embodiments also may be used to perform quality control types of inspections for the incoming composite material at the receiving dock. For example, performing an inspection of composite materials prior to the composite materials being placed onto tools or otherwise processed into a composite workpiece could identify contaminants on the composite material prior to using the composite material in the work stream. Additionally, the different illustrative embodiments also may be used to identify inconsistencies in the composite materials that are to be used to form a workpiece. As used herein, an "inconsistency", when used with reference to a composite material for use in forming a composite workpiece, may include a contaminant, disbonding in the composite material, delamination in the composite material, or other undesired conditions in the composite map. As a result, time and money may be saved by discovering a contaminant at this stage versus discovering the contaminant later during the manufacturing process.

In these illustrative examples, the inconsistency in the composite material for use when forming a workpiece may be on the surface of the composite material or located within the interior of the composite material. The image generated from the response to the electromagnetic radiation may include graphical indicators that indicate these inconsistencies. The graphical indicators may be selected to indicate the type of inconsistency that has been detected.

The illustrative embodiments provide a method and apparatus that allows for a reduction in the amount of time needed to manufacture parts for composite structures. As a result, the cost, time, or both the cost and the time for manufacturing a platform, such as an aircraft, may be reduced.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for inspecting a composite workpiece, the method comprising:
   separating a response to electromagnetic radiation directed to a surface of the composite workpiece into a number of wavelengths for each of a number of locations on the surface of the composite workpiece;
   identifying a set of contaminants not visible to a naked eye on the surface of the composite workpiece from the number of wavelengths for the each of the number of locations; and
   generating a two-dimensional image of the surface of the composite workpiece with a set of graphical indicators indicating the set of contaminants not visible to the naked eye identified from the number of wavelengths for the each of the number of locations on the surface of the composite workpiece.

2. The method of claim 1, wherein identifying the set of contaminants not visible to the naked eye on the surface of the composite workpiece from the number of wavelengths for the each of the number of locations comprises:
   identifying the set of contaminants not visible to the naked eye based on a comparison of the number of wavelengths for the each of the number of locations on the surface of the composite workpiece to a database of wavelengths for known contaminants.

3. The method of claim 1 further comprising:
   projecting the two-dimensional image with the set of graphical indicators onto the surface of the composite workpiece.

4. The method of claim 1, wherein generating the two-dimensional image of the surface of the composite workpiece with the set of graphical indicators indicating the set of contaminants not visible to the naked eye identified from the number of wavelengths for the each of the number of locations on the surface of the composite workpiece comprises:
   generating the two-dimensional image of the surface of the composite workpiece with a visible light sensor system; and
   including the set of graphical indicators indicating the set of contaminants not visible to the naked eye identified from the number of wavelengths for the each of the number of locations on the surface of the composite workpiece in the two-dimensional image in locations corresponding to the number of locations.

5. The method of claim 1, wherein the separating, identifying, and generating steps are performed when a number of layers of composite material are laid up for the composite workpiece.

6. The method of claim 5, wherein the separating, identifying, and generating steps are performed each time the number of layers of the composite material are laid up for the composite workpiece prior to curing the number of layers of composite material.

7. The method of claim 1, wherein the separating, identifying, and generating steps are performed prior to curing the composite workpiece.

8. The method of claim 1, wherein separating the response to the electromagnetic radiation directed to the surface of the composite workpiece into the number of wavelengths for the each of the number of locations on the surface of the composite workpiece comprises:
   scanning the response to the electromagnetic radiation across a filter, wherein the filter is configured to separate the response into the number of wavelengths and the filter is selected from the group consisting of an optical prism, a holographic grating, a conventional grating, and a wedge filter.

9. The method of claim 8, wherein the filter is the wedge filter and further comprises a length defining frequencies configured to be passed by the wedge filter, wherein the frequencies increase in a direction along the length.

10. The method of claim 1, wherein the electromagnetic radiation is generated by at least one of a halogen light system, a light emitting diode system, a xenon arc lamp system, a laser diode system, and a quartz lamp system.

11. The method of claim 1, wherein the composite workpiece forms a part for a platform selected from one of an aquatic-based structure, a space-based structure, a surface ship, a tank, a train, a spacecraft, a space station, a satellite, a submarine, an automobile, a power plant, a bridge, a dam, a manufacturing facility, and a building.

12. A method for inspecting a tool for laying up layers of composite material, the method comprising:
   separating a response to electromagnetic radiation directed to a surface of the tool into a number of wavelengths for each of a number of locations on the surface of the tool prior to laying up the layers of composite material on the surface of the tool;
   identifying a set of contaminants from the number of wavelengths for the each of the number of locations on the surface of the tool; and
   generating a two-dimensional image of the surface of the tool with a set of graphical indicators indicating the set of contaminants identified from the number of wavelengths for the each of the number of locations on the surface of the tool.

13. A method for inspecting a composite material, the method comprising:
- separating a response to infrared electromagnetic radiation directed to a surface of the composite material into a number of infrared wavelengths for each of a number of locations on the surface of the composite material;
- identifying a set of inconsistencies for the composite material from the number of infrared wavelengths for the each of the number of locations; and
- generating a two-dimensional image of the composite material with a set of graphical indicators indicating the set of inconsistencies identified from the number of infrared wavelengths for the each of the number of locations on the surface of the composite material.

14. The method of claim 13, wherein the set of inconsistencies comprises inconsistencies selected from the group consisting of voids and a porosity.

15. An apparatus comprising:
- a spectral sensor system configured to separate a response to electromagnetic radiation directed at a surface of a composite workpiece into a number of wavelengths comprising wavelengths outside of a visible light spectrum and generate data from the number of wavelengths of the electromagnetic radiation; and
- an analyzer configured to cause the spectral sensor system to generate the data from the response after a number of layers of composite material have been laid up for the composite workpiece and prior to the number of layers of composite material being cured, and to generate a two-dimensional image of the surface of the composite workpiece with a set of graphical indicators indicating a set of contaminants identified from the number of wavelengths for each of a number of locations on the surface of the composite workpiece.

16. The apparatus of claim 15 further comprising:
- a visible light sensor system configured to generate a visible light image of the surface of the composite workpiece, and wherein the analyzer is configured to include the set of graphical indicators indicating the set of contaminants identified from the number of wavelengths for the each of the number of locations on the surface of the composite workpiece in the visible light image in locations corresponding to the number of locations to form the two-dimensional image of the surface of the composite workpiece with the set of graphical indicators indicating the set of contaminants identified from the number of wavelengths for the each of the number of locations on the surface of the composite workpiece.

17. The apparatus of claim 15, wherein the spectral sensor system comprises:
- a filter configured to separate the response to the electromagnetic radiation directed at the surface of the composite workpiece into the number of wavelengths comprising the wavelengths outside of the visible light spectrum;
- a sensor array comprising sensors configured to generate the data from the number of wavelengths comprising the wavelengths outside of the visible light spectrum of the electromagnetic radiation separated in the response by the filter, wherein the sensors are selected from the group consisting of digital-charged-coupled-devices, complimentary metal oxide semiconductor devices, indium antimonide (InSb) semiconductor devices, and mercury cadmium telluride (HgCdTe) semiconductor devices; and
- wherein the number of wavelengths comprises a continuous range of wavelengths.

18. The apparatus of claim 17 further comprising:
- a director system comprising a moveable mirror system configured to cause the response to the electromagnetic radiation to be scanned across the filter; and
- an electromagnetic radiation source configured to generate the electromagnetic radiation and to pass coherent light through the moveable mirror system toward the surface of the composite workpiece.

19. The apparatus of claim 15, wherein the set of contaminants identified from the number of wavelengths for the each of the number of locations on the surface of the composite workpiece comprises contaminants selected from the group consisting of liquids, moisture, and plastic particles.

20. The apparatus of claim 15, wherein the analyzer is further configured to identify the set of contaminants by comparing the data to a signature database, wherein a signature in the signature database comprises an intensity for a wavelength in the number of wavelengths that is unique to a contaminant in the set of contaminants and wherein the data comprises at least one of intensities for the number of wavelengths, amplitudes for the number of wavelengths, and the wavelengths.

* * * * *